United States Patent
Kawase et al.

(10) Patent No.: US 6,453,724 B1
(45) Date of Patent: Sep. 24, 2002

(54) GAS CONCENTRATION SENSING APPARATUS

(75) Inventors: Tomoo Kawase, Nagoya; Eiichi Kurokawa, Okazaki; Satoshi Hada, Kariya; Toshiyuki Suzuki, Handa, all of (JP)

(73) Assignee: Denso Corporation (JP)

(*) Notice: Subject to any disclaimer, the term of this patent is extended or adjusted under 35 U.S.C. 154(b) by 0 days.

(21) Appl. No.: 09/399,949

(22) Filed: Sep. 20, 1999

(30) Foreign Application Priority Data

Sep. 29, 1998 (JP) .......................... 10-275521
Jul. 19, 1999 (JP) .......................... 11-204927

(51) Int. Cl.[7] .......................... G01N 7/00; G01N 33/497
(52) U.S. Cl. .................................... 73/23.31
(58) Field of Search .......................... 73/23.31, 23.2, 73/31.05, 23.32, 1.06; 204/425, 412, 426; 219/505, 553

(56) References Cited

U.S. PATENT DOCUMENTS

| | | | |
|---|---|---|---|
| 4,313,338 A | * 2/1982 | Abe et al. | 73/23 |
| 4,543,176 A | 9/1985 | Harada et al. | 204/406 |
| 4,824,549 A | * 4/1989 | Hamada et al. | 204/110 |
| 4,875,981 A | * 10/1989 | Usami et al. | 204/1 |
| 4,993,392 A | 2/1991 | Tanaka et al. | |
| 5,037,761 A | 8/1991 | Barnett et al. | |
| 5,291,417 A | 3/1994 | Schnaibel et al. | 364/482 |
| 5,476,001 A | * 12/1995 | Hoetzel et al. | 75/23.31 |
| 5,672,811 A | * 9/1997 | Kato et al. | 73/31.05 |
| 5,866,799 A | 2/1999 | Kato et al. | 73/31.05 |

FOREIGN PATENT DOCUMENTS

| | | |
|---|---|---|
| EP | 0 798 555 | 10/1997 |
| EP | 0 822 326 | 2/1998 |
| EP | 0 851 108 A2 | 7/1998 |
| EP | 0 851 225 | 7/1998 |
| EP | 0 859 232 | 8/1998 |
| EP | 0 984 275 A2 | 3/2000 |
| JP | 8-271476 | 10/1996 |
| JP | 9-318596 | 12/1997 |

* cited by examiner

*Primary Examiner*—Max Noori
*Assistant Examiner*—Octavia Davis
(74) *Attorney, Agent, or Firm*—Nixon & Vanderhye PC

(57) ABSTRACT

A gas concentration sensor comprises a pump cell for detecting an oxygen concentration in an exhaust gas and a sensor cell for detecting a NOx concentration in the exhaust gas. A porous diffusive layer is interposed between these cells. Furthermore, the sensor comprises a heater for heating these cells. A control circuit produces a sensor cell voltage having an A.C. component to detect the impedance of sensor cell. The electric power supplied to the heater is controlled based on a detected impedance value of the sensor cell.

14 Claims, 28 Drawing Sheets

GAS CONCENTRATION SENSING APPARATUS

BACKGROUND OF THE INVENTION

The present invention relates to a gas concentration sensing apparatus using a gas concentration sensor capable of detecting the concentration of a specific component contained in an exhaust gas emitted from an automotive engine.

Exhaust gases emitted from automotive engines cause the air pollution which induces serious problems in the modern society. To reduce the harmful or poisonous substances contained in the emission gases, the law regulations for emission gas purification standard have been becoming severe year by year. Thus, the study and development for suppressing the emission amount of harmful or poisonous substances contained in the exhaust gas has been steadily conducted through the improvement of combustion control for gasoline or diesel engines and the use of catalytic converters. The regulation OBD-II (on Board Diagnostic-II) is already introduced in the United States, according to which every purification system is required to check whether a catalytic converter is in an appropriate condition for purifying the emission gases.

There is a so-called 2 O2 sensor monitoring system including one O2 sensor disposed at an upstream side of a catalyst and another O2 sensor disposed at a downstream side. This system is, however, an indirect detecting system. No pollution substances are directly detectable by this system. In other words, it is impossible to accurately check wether the pollution substances in the exhaust gas are actually reduced.

If a combustion control monitoring or a catalyst monitoring becomes feasible by directly monitoring a NOx concentration in the exhaust gas, this will make it possible to accurately check the reduction of the pollution substances in the exhaust gas. Namely, if the fuel injection or the EGR rate is feedback controllable by a NOx concentration value detected from the exhaust gas, it will become possible to reduce the pollution substances emitted from engines. Furthermore, providing a NOx sensor at a downstream side of the catalytic converter is effective to easily check a deteriorated condition of a catalyst accommodated in the catalytic converter.

From the foregoing, it is desirable to provide a NOx sensor capable of accurately detecting the NOx concentration in the exhaust gas. And also, it is desirable to provide a technique for installing the NOx sensor in an automotive engine.

This kind of conventional technique is, for example, disclosed in the unexamined Japanese patent publication No. 8-271476 (corresponding to the U.S. Pat. No. 5,866,799) or in the unexamined Japanese patent publication No. 9-318596 (corresponding to the European Patent Application No. 798,555), according to which the oxygen concentration is reduced in advance to detect the NOx concentration. More specifically, a chamber is provided separately from the exhaust gas environment via a diffusive resistor. A pump cell discharges the oxygen (O2) from this chamber. A sensor cell decomposes and discharges the residual NOx. A current value obtainable from the sensor cell indirectly represents the NOx decomposition amount, i.e., the NOx concentration. To activate the NOx sensor, it is necessary to keep the temperatures of the pump cell and the sensor cell at a predetermined level or above so that the oxygen ion conductivity of a solid electrolytic element can be enhanced.

To this end, the NOx sensor comprises a heater provided in the vicinity of the pump cell and the sensor cell for warming up these cells.

Furthermore, when detecting the exhaust gas components, the NOx sensor is subjected to a large temperature fluctuation as well as a large gas flow fluctuation of the exhaust gas. Accordingly, to improve the accuracy of the NOx sensor, it is necessary to accurately control the temperature of the NOx sensor to a constant value.

For example, a first method for controlling a sensor temperature is to detect a heater resistance and control the sensor temperature in accordance with a detected heater resistance value. According to this method, a heater temperature is measured indirectly by measuring the heater resistance value. The measured temperature is regarded as being substantially equal to the cell temperature. And, the temperature control is performed so as to maintain the heater temperature at a constant level. A second method is to detect an internal impedance of a pump cell and control the sensor temperature in accordance with a detected internal impedance value. Usually, an impedance of the pump cell is detected to control the heater. For example, SAE-No. 970858 discloses a heater control of a sensor comprising first and second pump cells. According to this conventional heater control, an impedance of the second pump cell is detected and the heater is controlled based on a detected impedance value.

However, the above-described first method is inaccurate in controlling the sensor cell temperature when the exhaust gas temperature varies widely or the exhaust gas flow speed is high, because the cell temperature is different from the heater temperature in such conditions. Similarly, the above-described second method is inaccurate in controlling the sensor cell temperature when the exhaust gas temperature varies widely or the exhaust gas flow speed is high, because the pump cell temperature is different from the sensor cell temperature in such conditions.

Accordingly, the sensor cell temperature fluctuates and the NOx concentration sensing accuracy worsens. It is thus desirable to provide a sensing apparatus capable of accurately detecting a gas concentration regardless of the temperature fluctuation or gas flow speed change in the exhaust gas.

SUMMARY OF THE INVENTION

In view of the foregoing problems in the prior art, the present invention has an object to provide a gas concentration sensing apparatus which always assures an accurate gas concentration detection regardless of the temperature fluctuation or gas flow speed change in the measuring gas.

In order to accomplish this and other related objects, the present invention provides a gas concentration sensing apparatus using a gas concentration sensor comprising a first cell for discharging excessive oxygen contained in a measuring gas in accordance with an applied voltage and producing a current responsive to an oxygen concentration, a second cell producing a current responsive to a concentration of a specific component involved in the residual measuring gas after the excessive oxygen is discharged, and a heater for heating the first cell and the second cell. For example, when this gas concentration sensing apparatus is used to detect both the oxygen concentration and the NOx concentration in an exhaust gas, the first cell detects the oxygen concentration and the second cell detects the NOx concentration.

According to a first gas concentration sensing apparatus in accordance with the present invention, an internal resistance of the second cell is detected. And, electric power supplied to the heater is controlled in accordance with a detected internal resistance value of the second cell.

The above-described arrangement makes it possible to control the internal resistance of the second cell to a desired value constantly through the electric power control of the heater. Accordingly, it becomes possible to prevent the temperature of the second cell from being changed undesirably due to the temperature or flow speed fluctuation of the measuring gas (e.g., exhaust gas), thereby appropriately maintaining the NOx concentration sensing accuracy. Furthermore, as apparent from the characteristics shown in FIG. 6, the NOx concentration is detectable in a relatively narrow region (i.e., a flat region). The temperature variation of the second cell (e.g., a sensor cell) renders the sensor output unstable. However, the above-described heater power control ensures an accurate detection of the NOx concentration. As a result, the present invention makes it possible to always assure an accurate gas concentration detection regardless of the temperature fluctuation or the gas flow speed change of the measuring gas.

Preferably, an internal resistance of the first cell is also detected. And, the voltage applied to the first cell is controlled in accordance with a detected internal resistance value of the first cell.

As described above, when the heater power control is performed based on the internal resistance of the second cell (e.g., sensor cell), the temperature of the second cell (e.g., sensor cell) can be controlled to a constant value. However, the temperature of the first cell (e.g., pump cell) may vary in accordance with the temperature change of the measuring gas. To solve this problem, it is preferable to control the voltage applied to the first cell in accordance with the internal resistance of the first cell. This arrangement makes it possible to adequately manage the applied voltage. The oxygen concentration sensing accuracy can be maintained appropriately. The sensing accuracy of the NOx concentration is also improved in accordance with the improvement of the oxygen concentration sensing accuracy.

The present invention further provides a second gas concentration sensing apparatus using a gas concentration sensor comprising a plurality of cells including a first cell for discharging excessive oxygen contained in a measuring gas in accordance with an applied voltage and producing a current responsive to an oxygen concentration, and a second cell producing a current responsive to a concentration of a specific component involved in the residual measuring gas after the excessive oxygen is discharged, and a heater for heating the plurality of cells. The second gas concentration sensing apparatus is characterized by detecting means for detecting an internal resistance of each of the plurality of cells, judging means for judging temperature conditions of the plurality of cells, and power control means for selectively performing a heater power control based on a detected internal resistance value with reference to the judgement result of the temperature conditions.

Selectively performing the heater power control based on the internal resistance of the plurality of cells makes it possible to suppress the deterioration of the sensing accuracy in the gas concentration detection. Thus, the gas concentration sensing accuracy can be maintained adequately even when respective cells have temperatures different from each other due to their structures.

Practically, it is desirable that, in a cold startup condition, the heater power control is performed based on a detected internal resistance value of a highest temperature cell among the plurality of cells. And thereafter, the heater power control is performed based on a detected internal resistance value of the second cell. Alternatively, it is desirable that the heater power control is performed based on a detected internal resistance value of a highest temperature cell among the plurality of cells when there is a large temperature difference among the plurality of cells. And, the heater power control is performed based on a detected internal resistance value of the second cell when there is a small temperature difference among the plurality of cells.

According to this arrangement, when the temperature of the measuring gas (e.g., exhaust gas) is stable, the heater power control is performed based on the internal resistance of the second cell. When the temperature of the measuring gas is temporarily increased, the heater power control is performed based on the internal resistance of the cell having the highest cell. Hence, it becomes possible to adequately maintain the gas concentration sensing accuracy even when the ce; temperature distribution varies.

A third gas concentration sensing apparatus in accordance with the present invention comprises first detecting means for detecting an internal resistance of the first cell, second detecting means for detecting an internal resistance of the second cell, and power control means for controlling electric power supplied to the heater so as to equalize a sum or an average of detected internal resistance values of the first and second cells with a target value.

In this case, even when the temperature distribution varies in each cell, the temperature difference can be reduced effectively. As a result, it becomes possible to maintain each cell in an appropriate temperature zone so as not to be excessively heated or cooled, thereby enabling a stable gas concentration detection.

The second or third gas concentration sensing apparatus may further comprise voltage control means for controlling the voltage applied to the first cell based on the detected internal resistance value of the first cell. In this case, it is preferable to control the voltage applied to the first cell in accordance with the detected internal resistance value of the first cell. The applied voltage can be adequately managed. The oxygen concentration sensing accuracy can be maintained appropriately.

In the first to third gas concentration sensing apparatus, the internal resistance of each cell is detected by temporarily changing the voltage or current applied to each cell. A sample hold circuit is provided in a signal path for outputting a sensor signal representing a detected oxygen or other gas concentration in the measuring gas. The sample hold circuit holds a latest value of the sensor signal during the internal resistance detection of each cell.

Namely, the gas concentration sensing apparatus temporarily changes the voltage applied to respective cells including the first and second cells to detect their internal resistance values. Such a voltage change may cause an interference of currents flowing through respective cells. The output signal representing a detected gas concentration may fluctuate undesirably. To solve this problem, the present invention provides the sample hold circuit for holding the latest value of the sensor signal during the internal resistance detection of each cell.

The first to third gas concentration sensing apparatus may further comprise speed limiting means for limiting a change speed of the voltage applied to each cell. This is effective to suppress the oscillation of the applied voltage.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
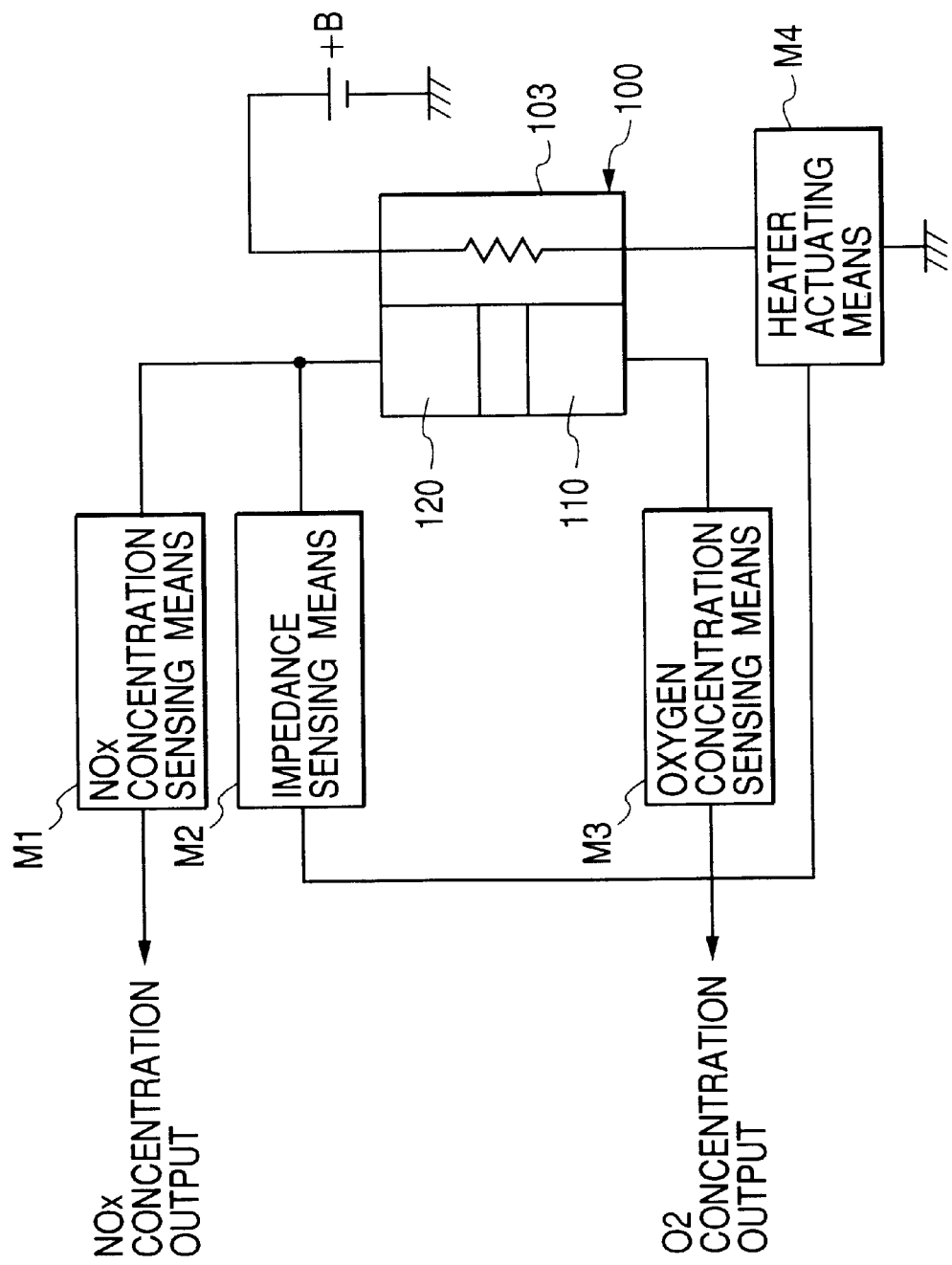
FIG. 1 is a block diagram showing a fundamental arrangement of a gas concentration sensing apparatus in accordance with the present invention.

Preferred embodiments of the present invention will be explained in greater detail hereinafter with reference to the accompanying drawings. Identical parts are denoted by the same reference numerals throughout the views.

First Embodiment

A first embodiment of the present invention will be explained with reference to attached drawings. A gas concentration sensing apparatus of the first embodiment is applicable to a gasoline engine for an automotive vehicle. An air-fuel ratio control system, incorporated in this engine, performs a feedback control for obtaining a desirable air-fuel ratio (A/F) by controlling a fuel injection amount supplied to the engine based on a detected value of the gas concentration sensing apparatus. The first embodiment obtains gas concentration data from a so-called combined or composite gas sensor. The combined gas sensor is capable of simultaneously detecting an oxygen concentration and a NOx concentration from an exhaust gas.

More specifically, the gas concentration sensing apparatus of the first embodiment performs an air-fuel ratio feedback control based on a detected oxygen concentration, and also controls a NOx catalyst (e.g., NOx adsorbable and reducible catalyst) installed in an engine exhaust pipe in accordance with a detected NOx concentration. The NOx catalyst control is performed in the following manner. Some of NOx gas is discharged without being purified by the NOx catalyst. This amount can be indirectly judged from the detected value of a gas concentration sensor. When an increase of a non-purified NOx amount is detected, the reconstructive processing is performed to restore the NOx purification ability. For example, a rich gas is temporarily supplied to the NOx catalyst to remove the adsorbed ions from the catalyst.

FIG. 1 shows a schematic arrangement of a gas concentration sensing apparatus in accordance with the first embodiment. A gas concentration sensor 100 comprises a pump cell 110 detecting an oxygen concentration, a sensor cell 120 detecting a NOx concentration, and a heater 103 generating heat in response to electric power supplied from a +B terminal of a battery source. A NOx concentration sensing means M1 is connected to a sensor cell electrode of the gas concentration sensor 100 for applying a voltage to the sensor cell 120 to generate a current signal responsive to a detected NOx concentration and for sending the produced current signal to an external device. An impedance sensing means M2 is also connected to the sensor cell electrode for detecting a current value corresponding to an impedance of the sensor cell 120 and for sending an actuation signal to the heater 103 so that the impedance of the sensor cell 120 is equalized to a predetermined target value.

An oxygen concentration sensing means M3 is connected to a pump cell electrode of the gas concentration sensor 100 for applying a voltage to the pump cell 110 to detect a current signal responsive to a detected oxygen concentration and for sending the produced current signal to an external device. A heater actuating means M4 is provided for actuating the heater 103 in accordance with the signal produced from the impedance sensing means M2.

Figure 3:
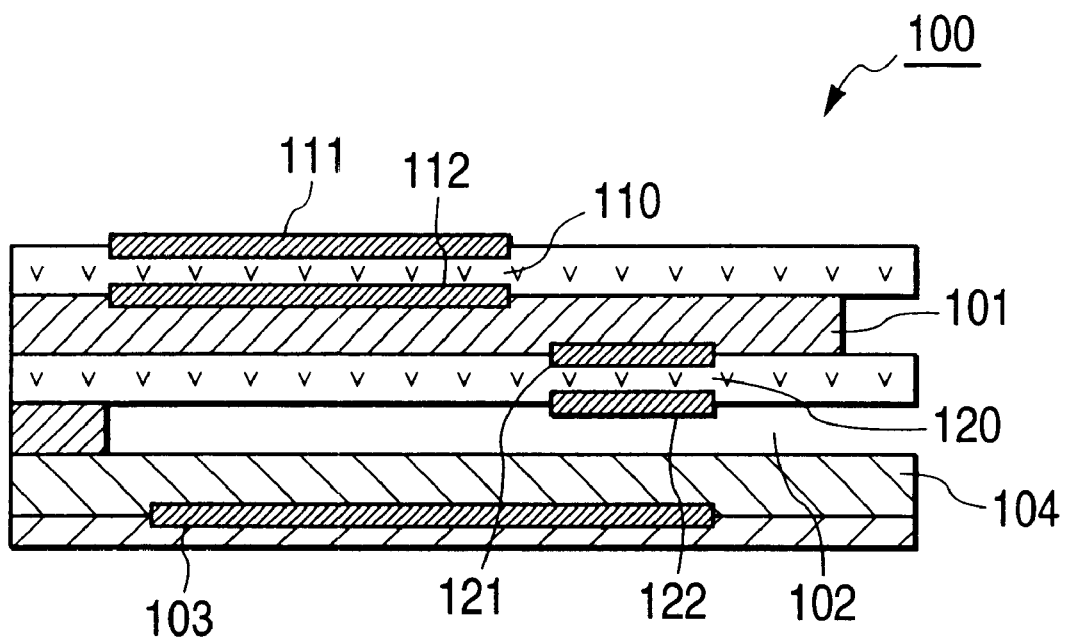
FIG. 3 is a cross-sectional view showing an essential arrangement of a gas concentration sensor in accordance with the first embodiment of the present invention.

Hereinafter, a detailed arrangement of a gas concentration sensing apparatus will be explained. FIG. 3 shows an arrangement of the gas concentration sensor 100. The gas concentration sensor 100 is a so-called combined or composite gas sensor having a double cell arrangement capable of simultaneously detecting both of the NOx concentration and the oxygen concentration. The gas concentration sensor 100 comprises the pump cell 110, a porous diffusive layer 101, the sensor cell 120, and an atmospheric duct 102 and the heater 103, which are stacked or laminated integrally. The gas concentration sensor 100 is installed to an engine exhaust pipe at its right end shown in FIG. 3. Thus, not only the upper and lower surfaces but the left surface of the sensor 100 are exposed to the exhaust gas.

More specifically, the pump cell is brought into contact with the porous diffusive layer 101 at one side and is exposed to the exhaust gas at the other side. A first pump electrode 111, provided on an upper surface of the pump cell 110, is exposed to the exhaust gas. A second pump electrode 112 is interposed between a lower surface of the pump cell 110 and an upper surface of the porous diffusive layer 101. The sensor cell 120 is located between the porous diffusive layer 101 and the atmospheric duct 102. A first sensor electrode 121, provided on an upper surface of the sensor cell 120, contacts with the lower surface of the porous diffusive layer 101. A second sensor electrode 122, provided on a lower surface of the sensor cell 120, faces to the atmospheric duct 102. The exhaust gas, introduced from the left end of the porous diffusive layer 101, flows in this porous diffusive layer 101 toward the right end thereof.

Each of the pump cell 110 and the sensor cell 120 comprises a solid electrolytic element. The solid electrolytic element is made of a sintered oxide material having appropriate oxygen ion conductivity. For example, the sintered oxide material comprises abase material, such as ZrO2, HfO2, ThO2, and Bi2O3, mixed with a solid soluble stabilizing material, such as CaO, MgO, Y2O3, and Yb2O3. The porous diffusive layer 101 is a heat-resistant inorganic material such as alumina, magnesia, quartzite, spinel, and mullite.

A precious metal having adequate catalytic activity, such as platinum Pt, is preferably used to form the first pump electrode 111 of the pump cell 110 and the first and second sensor electrodes 121 and 122 of the sensor cell 120. A precious metal which is inactive to a NOx gas (unable to decompose the NOx gas), such as Au-Pt, is preferably used to form the second pump electrode 112 of the pump cell 110 provided adjacent to the porous diffusive layer 101.

The heater 103 is embedded in an insulation layer 104. The atmospheric duct 102, serving as a reference gas chamber, is located between the insulation layer 104 and the sensor cell 120. External air, introduced into the atmospheric duct 102, serves as a reference gas providing a standard oxygen concentration. The insulation layer 104 is formed by an alumina member or the like. The heater 103 is formed by a cermet including platinum and alumina components. The heater 103 generates thermal energy in response to electric power supplied from an external power source to activate the sensor body including the pump cell 110 and the sensor cell 120 (as well as the electrodes). The heater 103 has a flat and extended heat generating portion so that a uniform sensor temperature distribution can be realized by thoroughly heating the pump cell 110 and the sensor cell 120.

Figure 4A:
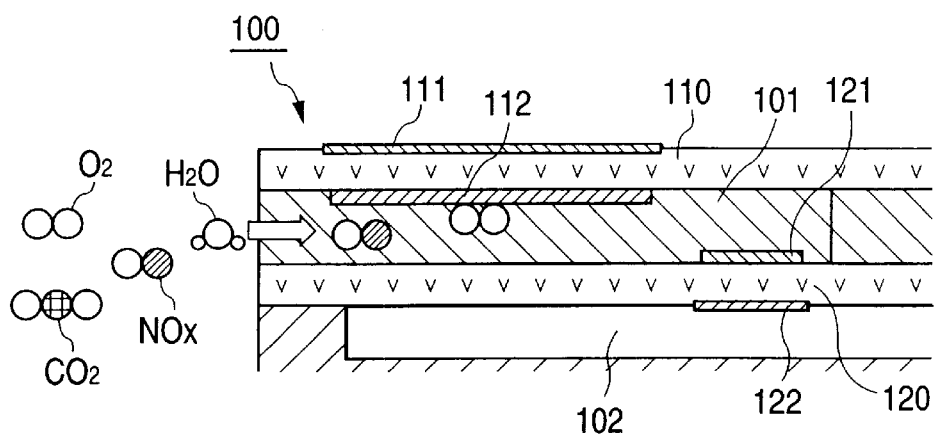
FIGS. 4A to 4C are views illustrating an operational principle of the gas concentration sensor in accordance with the first embodiment of the present invention.
Figure 4B:
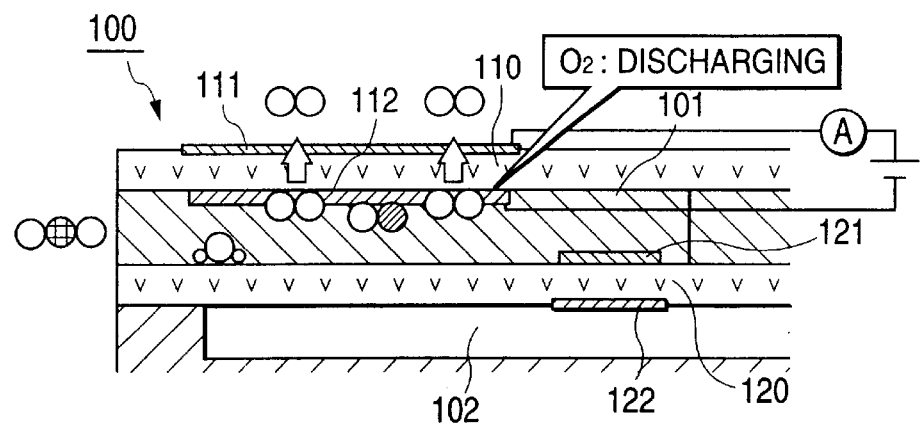
Figure 4C:
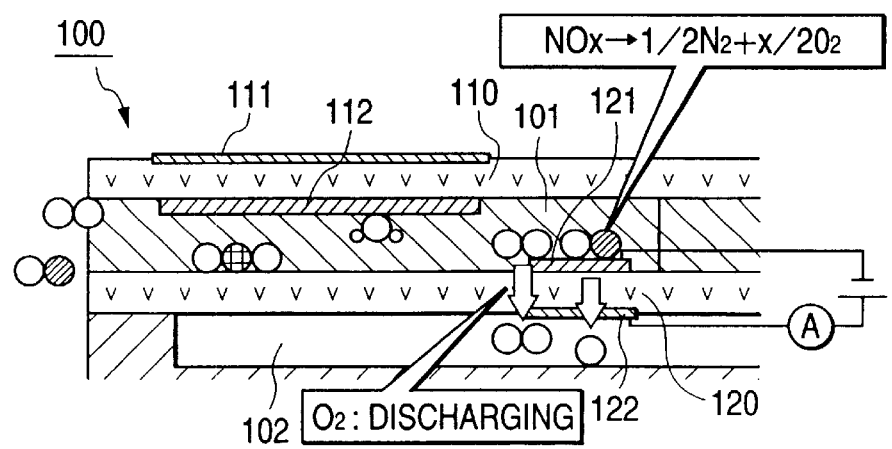

FIGS. 4A to 4C explain the operation of the above-described gas concentration sensor 100. As shown in FIG. 4A, exhaust gas components enter into the porous diffusive layer 101 from the left end. When the exhaust gas passes near the pump cell 110, the exhaust gas components are decomposed in response to the voltage applied to the pump cell 110. The exhaust gas contains gas components of oxygen (O2), nitrogen oxides (NOx), carbon dioxide (CO2), and water (H2O).

As described above, the second pump electrode 112 of the pump cell 110 is formed by a NOx inactive electrode (which is unable to decompose the NOx gas). Accordingly, as shown in FIG. 4B, the pump cell 110 decomposes only the oxygen (O2) component from the exhaust gas. The decomposed oxygen component is discharged through the first pump electrode 111 into the exhaust gas. The current flowing in the pump cell 110 during the discharge phenomenon is detectable as an indicia representing an oxygen concentration of the exhaust gas.

The pump cell 110 cannot decompose all of the oxygen (O2) in the exhaust gas. Thus, part of the undecomposed oxygen components continuously flows and will reach the sensor cell 120, where the residual oxygen (O2) and the NOx are decomposed by applying the voltage to the sensor cell 120 as shown in FIG. 4C. Namely, both of O2 and NOx are decomposed on the first sensor electrode 121 of the sensor cell 120. The decomposed components move across the sensor cell 120 and are discharged from the second sensor electrode 122 into the atmospheric duct 102. The current flowing in the sensor cell 120 during the discharge phenomenon is detectable as an indicia representing a NOx concentration of the exhaust gas.

Figure 5:
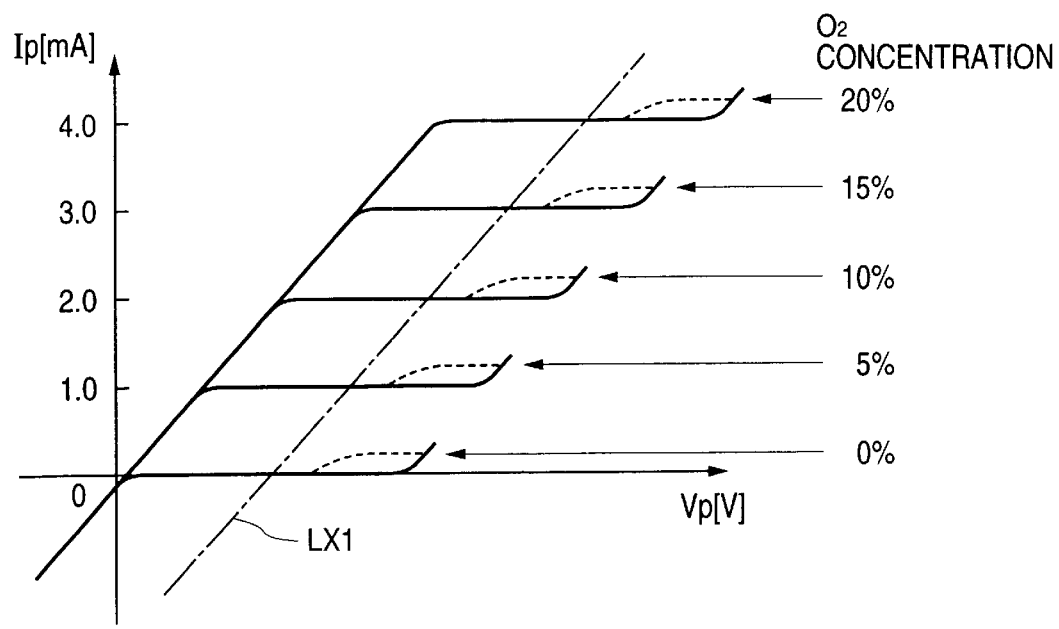
FIG. 5 is a V-I characteristic graph showing the pump cell characteristics of a gas concentration sensor.
Figure 6:
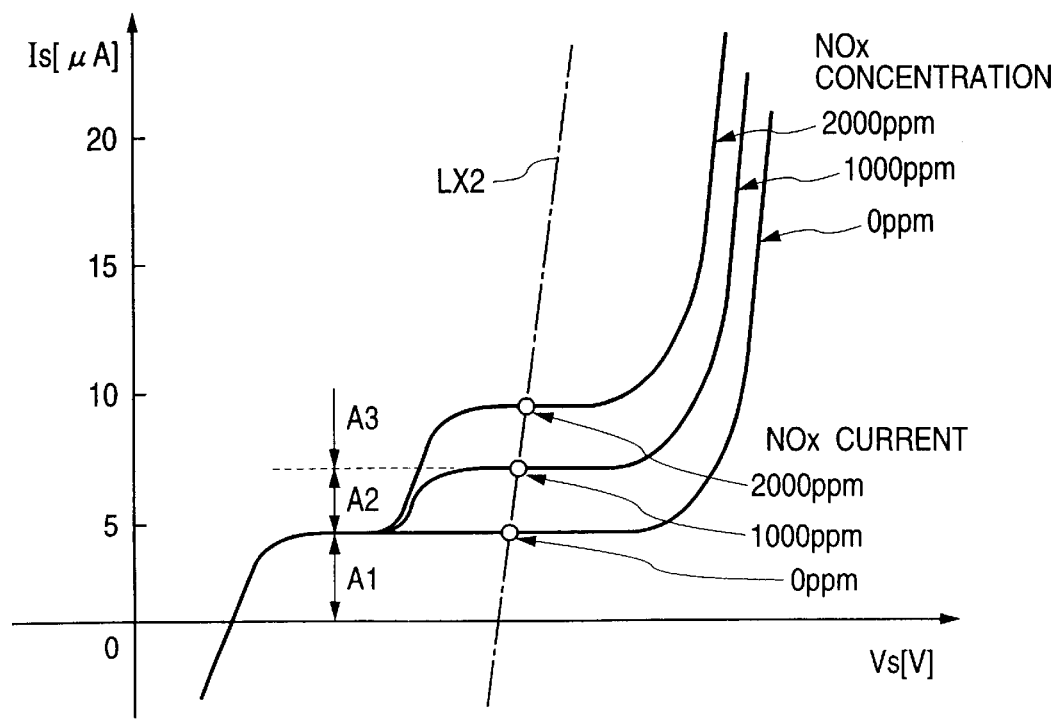
FIG. 6 is a V-I characteristic graph showing the sensor cell characteristics of a gas concentration sensor.

FIG. 5 shows the characteristics of the pump cell 110 in the oxygen concentration sensing operation. FIG. 6 shows the characteristic of the sensor cell 120 in the NOx concentration sensing operation. First, the pump cell characteristics will be explained with reference to FIG. 5.

As apparent from the V-I characteristic shown in FIG. 5, the pump cell has the limit-current characteristics in relation to the oxygen concentration. The abscissa represents a voltage Vp applied to the pump cell, and the ordinate represents a current Ip flowing through the pump cell. In FIG. 5, the limit current is sensible at a straight line region parallel to the V axis. The limit-current sensible region shifts toward the higher voltage side with increasing oxygen concentration.

When a fixed voltage is constantly applied regardless of a variation of oxygen concentration, it is not possible to accurately detect the oxygen concentration in the above-described limit-current sensible region (i.e., the straight-line portion parallel to the V axis). It means that the pump cell 110 cannot discharge a sufficient amount of oxygen. The sensor cell 120 will be subjected to an increased amount of residual oxygen. This may induce an error current in the detection of the NOx concentration.

To solve this problem, the voltage control is performed so that the applied voltage increases with an inclination equivalent to that of a D.C. resistance component (i.e., an inclined portion increasing in proportion to an applied voltage). Namely, the applied voltage is changed with reference to an application voltage line LX1 shown in FIG. 5, so that the desirable sensor current (i.e., limit current) can be detected regardless of the oxygen concentration in the exhaust gas. As the second pump electrode 112 of the pump cell 110 (facing to the porous diffusive layer 101) is a NOx inactive electrode, no NOx gas is decomposed at the pump cell 110. However, when the applied voltage exceeds a predetermined value, the NOx decomposition begins as shown in FIG. 5. Thus, the obtainable pump cell current is responsive to both of the oxygen concentration and the NOx concentration (refer to each dotted line portion in FIG. 5). Accordingly, the application voltage line LX1 is set so as not to cross with the NOx decomposing regions (dotted line portions).

Next, the sensor cell characteristics will be explained with reference to FIG. 6. As apparent from the V-I characteristic shown in FIG. 6, the sensor cell has the limit-current characteristics in relation to the NOx concentration. The abscissa represents a voltage Vs applied to the sensor cell, and the ordinate represents a current Is flowing through the sensor cell. In FIG. 6, A1 represents an offset current produced due to a residual oxygen flowing into the sensor cell 120 via the porous diffusive layer 101. A2 represents a NOx decomposition current. A3 represents a H2O decomposition current. A current value "A1+A2" represents a limit current corresponding to the NOx concentration in the exhaust gas. The limit-current sensible region, defining the NOx decomposition current, is a straight-line portion parallel to the V axis. The limit-current sensible region slightly shifts toward the higher voltage side with increasing NOx concentration. To solve this problem, the voltage control is performed so that the applied voltage is controlled so as to increase according to an application voltage line LX2 shown in FIG. 6. The desirable sensor current (i.e., limit current) is detectable regardless of the NOx concentration in the exhaust gas.

Figure 7A:
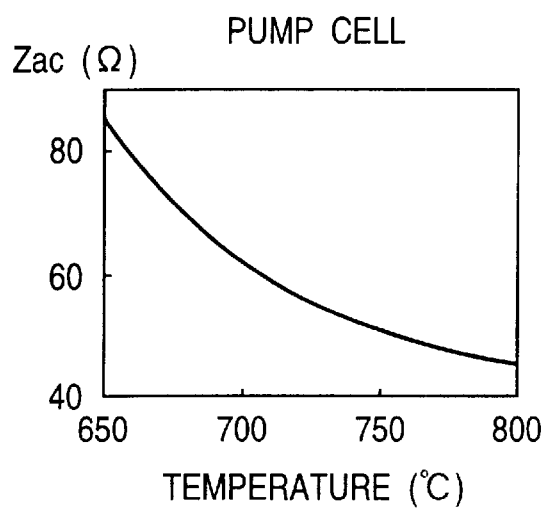
FIGS. 7A and 7B are graphs showing the temperature characteristics of a pump cell and a sensor cell.
Figure 7B:
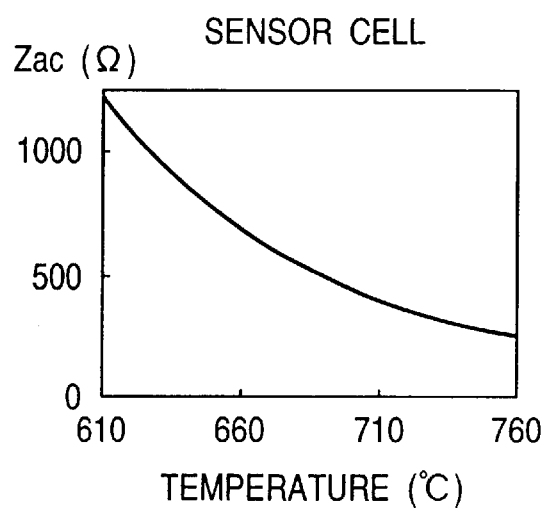

The temperature characteristics of the gas concentration sensor 100 will be explained. FIG. 7A shows a relationship between a cell temperature (° C.) and an A.C. impedance Zac (Ω) in a pump cell. FIG. 7B shows a relationship between a cell temperature (° C.) and an A.C. impedance Zac (Ω) in a sensor cell. As apparent from FIGS. 7A and 7B, each cell shows a correlation between the cell temperature and the A.C. impedance.

Figure 8:
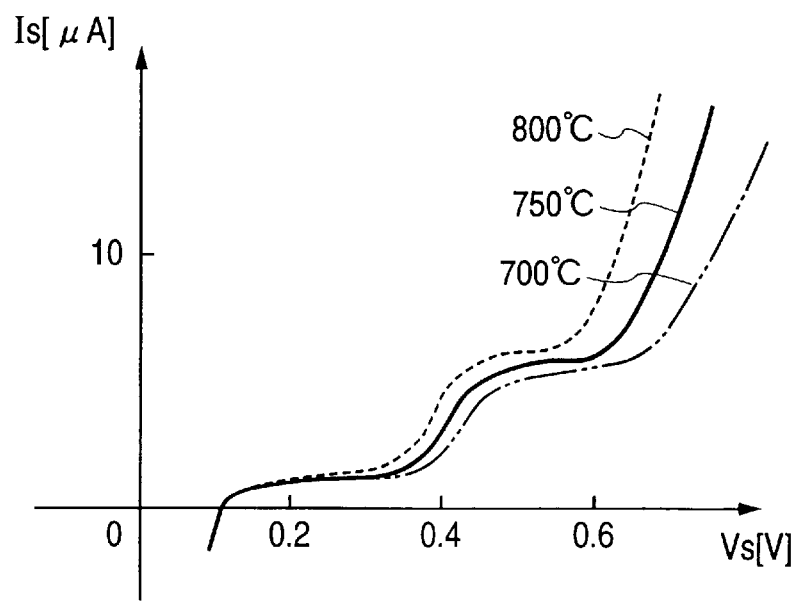
FIG. 8 is a V-I characteristic graph illustrating the temperature dependency of the sensor cell.

FIG. 8 shows the temperature dependency of a sensor cell. As apparent from this sensor characteristics, the sensor cell for detecting the NOx concentration has a temperature dependency. The limit current sensible region (i.e., flat region), representing the sensitivity of the NOx signal, is very narrow. Hence, the sensor output representing NOx concentration may vary largely and become unstable. Accordingly, to maintain the NOx concentration sensing accuracy at an appropriate level, it is inevitably necessary to accurately detect the sensor cell impedance and perform the heat control so as to equalize the impedance value to a constant value.

Figure 2:
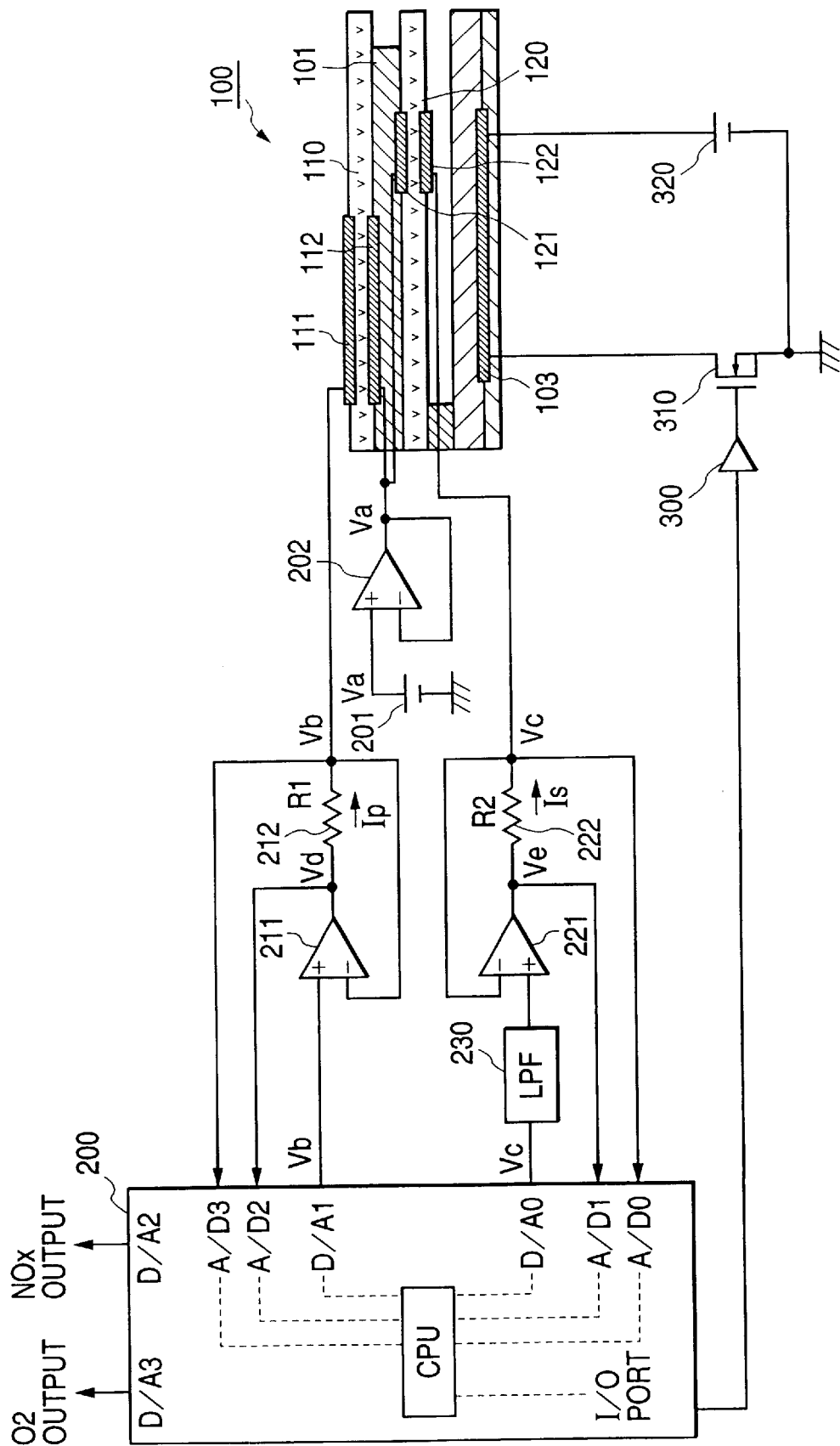
FIG. 2 is a diagram showing an overall arrangement of a gas concentration sensing apparatus in accordance with a first embodiment of the present invention.

FIG. 2 shows a detailed arrangement of the gas concentration sensing apparatus shown in FIG. 1. A lean gas is introduced into the porous diffusive layer 101 of the gas concentration sensor 100. Excessive oxygen is discharged from the porous diffusive layer 101 via the pump cell 110. The flow direction of pump cell current Ip at this moment defines a positive terminal and a negative terminal of the pump cell 110. Namely, the terminal connected to the first pump electrode 111 serves as a positive terminal. The terminal connected to the second pump electrode 112 serves as a negative terminal. In the same manner, the flow direction of sensor cell current Is at the moment the lean gas is introduced into the porous diffusive layer 101 defines the positive and negative terminals of the sensor cell 120. Namely, the terminal connected to the second sensor electrode 122 serves as a positive terminal. The terminal connected to the first sensor electrode 121 serves as a negative terminal.

A reference voltage circuit 201 and an amplification circuit 202 are connected to the common negative terminal of the pump cell 110 and the sensor cell 120. The reference voltage circuit 201 produces a voltage Va which is supplied to a non-inverting input terminal of the amplification circuit 202. An output terminal of the amplification circuit 202 is connected to an inverting input terminal of the amplification circuit 202 so as to constitute a voltage-follower arrangement. Thus, the voltage Va of the reference voltage circuit 201 is applied to the second pump electrode 112 (i.e., negative terminal of pump cell 110) and to the first sensor electrode 121 (i.e., negative terminal of sensor cell 120). With this arrangement, an electric potential of the common negative terminal of respective cells 110 and 120 is maintained at the reference voltage Va higher than a GND voltage (0V).

A control circuit 200 is a microcomputer comprising a CPU and A/D and D/A converters. A/D converters (i.e., A/D0 to A/D3) receive the voltages of terminals Vc, Ve, Vd and Vb, respectively. D/A converters (i.e., D/A1 and D/A0) produce a pump command voltage Vb and a sensor command voltage Vc, respectively. Another D/A converters (i.e., D/A2 and D/A3) produce a NOx concentration signal and an oxygen concentration signal, respectively.

The pump command voltage Vb, produced from the converter D/A1, is supplied to the non-inverting input terminal of the amplification circuit 211. An output terminal of the amplification circuit 211 is connected to one terminal of a current detecting resistor 212 which is provided to detect the pump cell current Ip responsive to the oxygen concentration. The other terminal of the current detecting resistor 212 is connected to the first pump electrode 111 (i.e., positive pump cell terminal) of the gas concentration sensor 100, and is also connected to the inverting input terminal of the amplification circuit 211. The converters A/D2 and A/D3 of the control circuit 200 are connected to the terminals of the current detecting resistor 212, respectively. With this arrangement, an electric potential of first pump electrode 111 is controlled to be always equalized to the pump command voltage Vb.

Accordingly, in response to the pump command voltage Vb fed from the converter D/A1 to the pump cell 110, the current detecting resistor 212 has terminal voltage Vd and Vb at both ends thereof. When R1 represents a resistance value of the current detecting resistor 212, the pump cell current Ip (i.e., oxygen concentration) is expressed by the following equation.

$$Ip=(Vd-Vb)/R1$$

The control circuit 200, the amplification circuit 211, and the current detecting resistor 212 cooperatively function as the oxygen concentration sensing means M3 shown in FIG. 1.

Meanwhile, the sensor command voltage Vc generated from the convertor D/A0 of the control circuit 200 is supplied to the non-inverting input terminal of an amplification circuit 221 via a LPF (i.e., low-pass filter) 230, such as a linear filter consisting of a resistor and a capacitor. An output terminal of the amplification circuit 221 is connected to one terminal of a current detecting resistor 222 which is provided to detect the sensor cell current Is responsive to the NOx concentration. The other terminal of the current detecting resistor 222 is connected to the second sensor electrode 122 (i.e., positive sensor cell terminal) of the gas concentration sensor 100, and is also connected to the inverting input terminal of the amplification circuit 221. The converters A/D0 and A/D1 of the control circuit 200 are connected to the terminals of the current detecting resistor 222, respectively. With this arrangement, an electric potential of second sensor electrode 122 is controlled to be always equalized to the sensor command voltage Vc.

Accordingly, in response to the sensor command voltage Vc fed from the converter D/A0 to the sensor cell 120, the current detecting resistor 222 has terminal voltage Ve and Vc at both ends thereof. When R2 represents a resistance value of the current detecting resistor 222, the sensor cell current Is (i.e., Nox concentration) is expressed by the following equation.

$$Is=(Ve-Vc)/R2$$

The control circuit 200, the amplification circuit 221, and the current detecting resistor 222 cooperatively function as the NOx concentration sensing means M1 shown in FIG. 1.

Furthermore, the control circuit 200 detects an A.C. impedance of sensor cell 120 based on the sweep method. Namely, during the impedance detection of sensor cell 120, the control circuit 200 changes the voltage applied to the sensor cell 120 instantaneously through the converter D/A0. The applied voltage is modified into a sine wave form through LPF 230 and applied to the sensor cell 120. A desirable A.C. voltage frequency is 10 kHz or above. The time constant of LPF 230 is set to approximately 5 μs. The converters A/D1 and A/D0 detect the changes of terminal voltages Ve and Vc at the both ends of current detecting resistor 222, respectively. The A.C. impedance of sensor cell 120 can be calculated based on the voltage change amount and the current change amount thus obtained.

In the control circuit 200, CPU generates a control command Duty through its I/O port to actuate a MOSFET driver 300. The MOSFET driver 300 controls a MOSFET 310 so as to perform a PWM control in accordance with the control command Duty. Through this PWM control, a controlled electric power is supplied from a power source 320 (e.g., a battery) to the heater 103.

Figure 9:
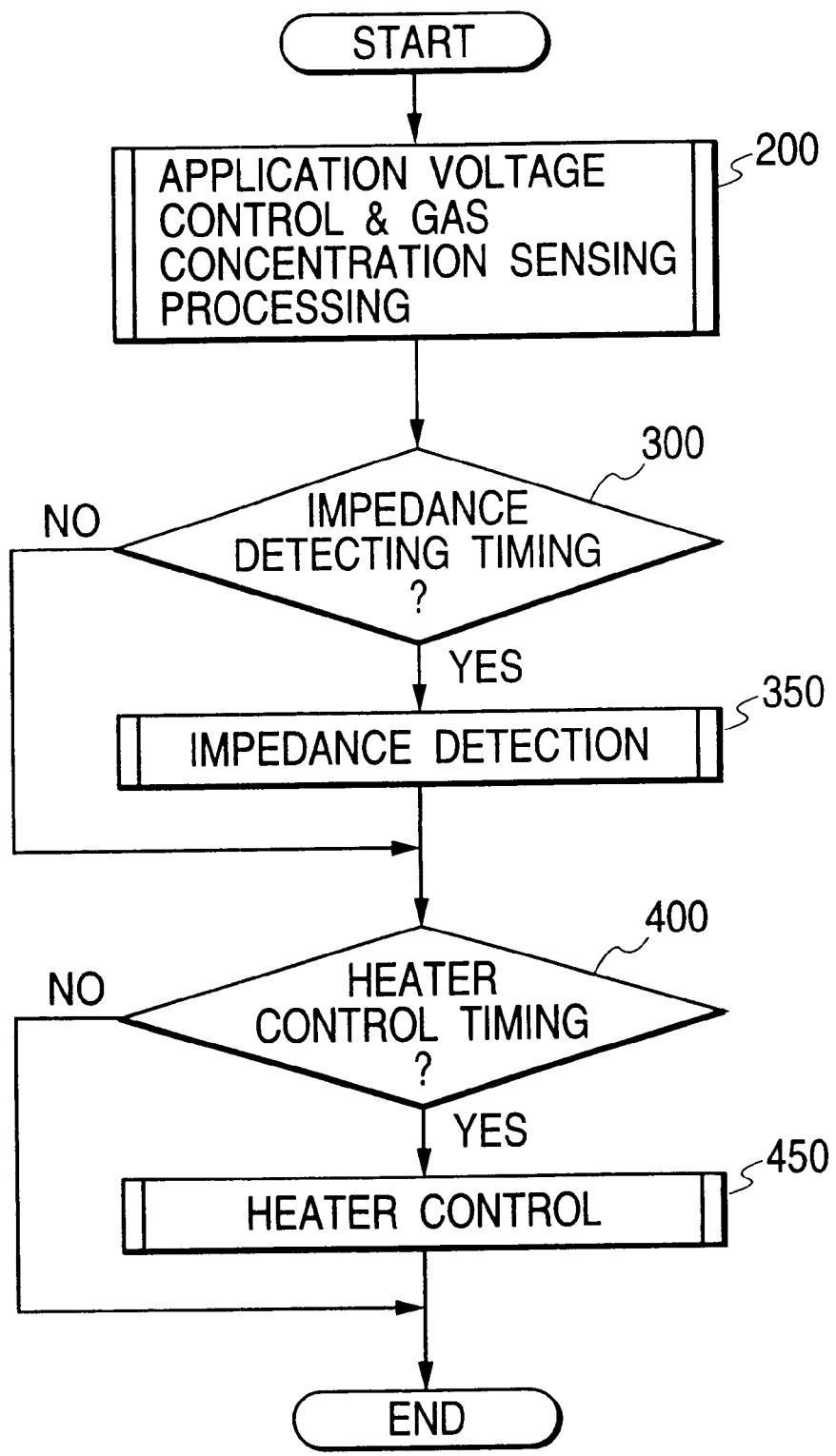
FIG. 9 is a flowchart showing a main routine performed in a control circuit of the gas concentration sensing apparatus in accordance with the first embodiment of the present invention.

FIGS. 9 through 12 are flowcharts explaining the control processing performed in the control circuit 200. FIG. 9 shows a main routine performed in the CPU of control circuit 200 at predetermined time intervals (e.g., 4 msec).

In FIG. 9, step 200 performs the application voltage control and the gas concentration sensing processing. The voltage applied to the gas concentration sensor 100 is controlled in accordance with a later-described processing procedure shown in FIG. 10. Step 300 checks whether an impedance detecting timing for the gas concentration sensor 100 has come or not. For example, when a predetermined time has passed from the previous impedance detection, the judgement result in step 300 becomes YES and the control flow proceeds to step 350. An appropriate impedance detecting interval may be 128 msec in an engine startup condition and will be extendable to 256 msec in a stationary driving condition.

Step 350 performs the impedance detection in accordance with a later-described processing procedure shown in FIG. 11. Step 400 checks whether a heater control timing for the gas concentration sensor 100 has come or not. For example, when a predetermined time (e.g., 128 msec) has passed from the previous heater control, the judgement result in step 400 becomes YES and the control flow proceeds to step 450 wherein the heater control is performed in accordance with a later-described processing procedure shown in FIG. 12.

Figure 10:
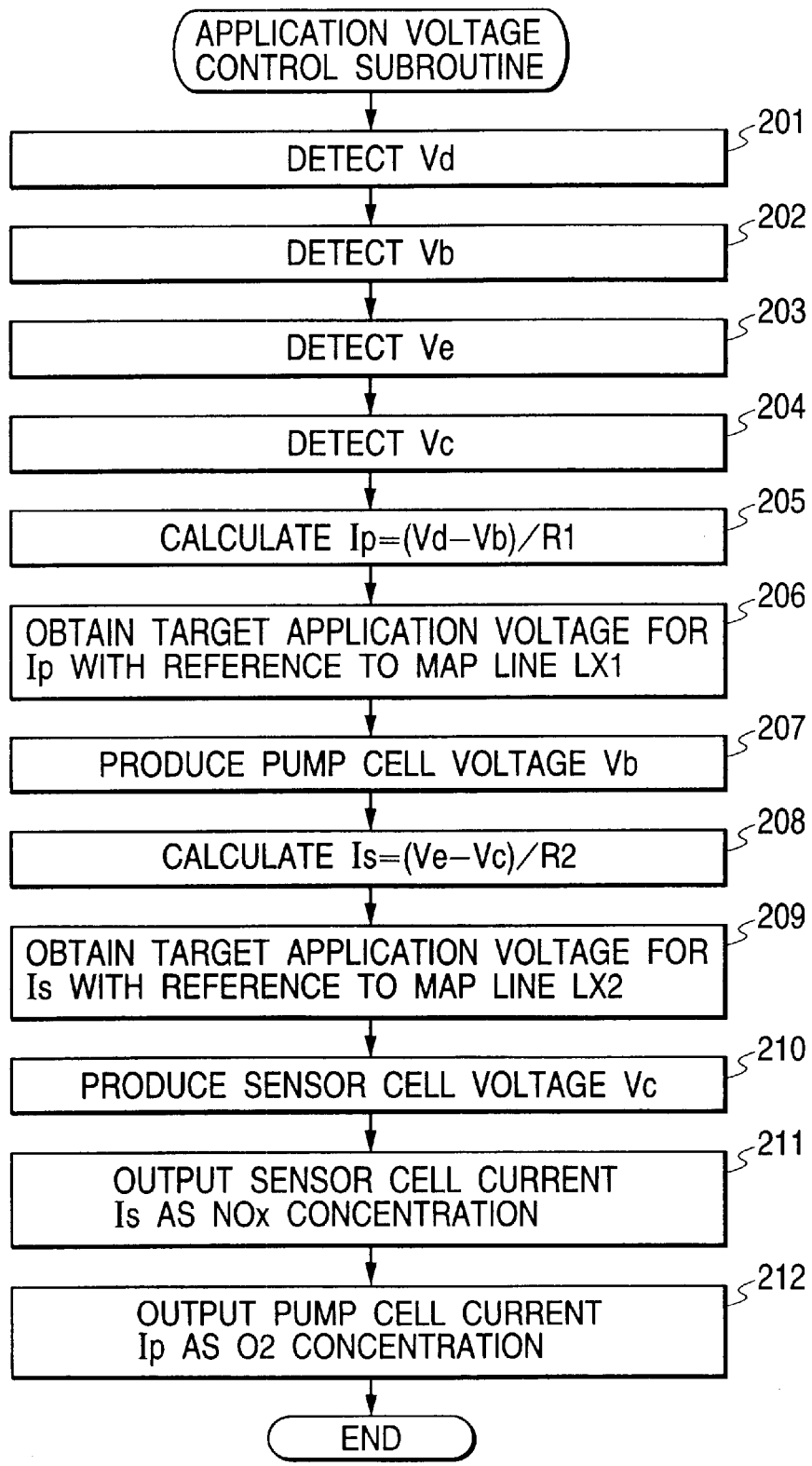
FIG. 10 is flowchart showing an application voltage control subroutine in accordance with the first embodiment of the present invention.

The application voltage control shown in step 200 will be explained with reference to the flowchart shown in FIG. 10. Steps 201 and 202 detect terminal voltages Vd and Vb at the terminals of the current detecting resistor 212 through the convertors A/D2 and A/D3, respectively. Next, steps 203 and 204 detect terminal voltages Ve and Vc at the terminals of the current detecting resistor 222 through the convertors A/D1 and A/D0, respectively.

Step 205 calculates the pump cell current Ip. Step 206 obtains a target application voltage for obtaining the calculated pump cell current Ip with reference to the application voltage line LX1 shown in FIG. 5. Namely, the target application voltage is obtained through a map calculation. Step 207 outputs the obtained target application voltage through the converter D/A1 as the command voltage Vb. Next, step 208 calculates the sensor cell current Is. Step 209 obtains a target application voltage for obtaining the calculated sensor cell current Is with reference to the application voltage line LX2 shown in FIG. 6. Namely, the target application voltage is obtained through a map calculation. Step 210 outputs the obtained target application voltage through the converter D/A0 as the command voltage Vc.

Then, step 211 outputs the calculated sensor cell current Is through the converter D/A2. The sensor cell current Is sent, as a current value representing the NOx concentration, to an engine control microcomputer or other external device. Finally, step 212 outputs the calculated pump cell current Ip through the converter D/A3. The pump cell current Ip is sent, as a current value representing the oxygen concentration, to the engine control microcomputer or other external device. In this case, the serial communication will be used to perform the steps 211 and 212 for outputting the gas concentration signals.

Figure 13:
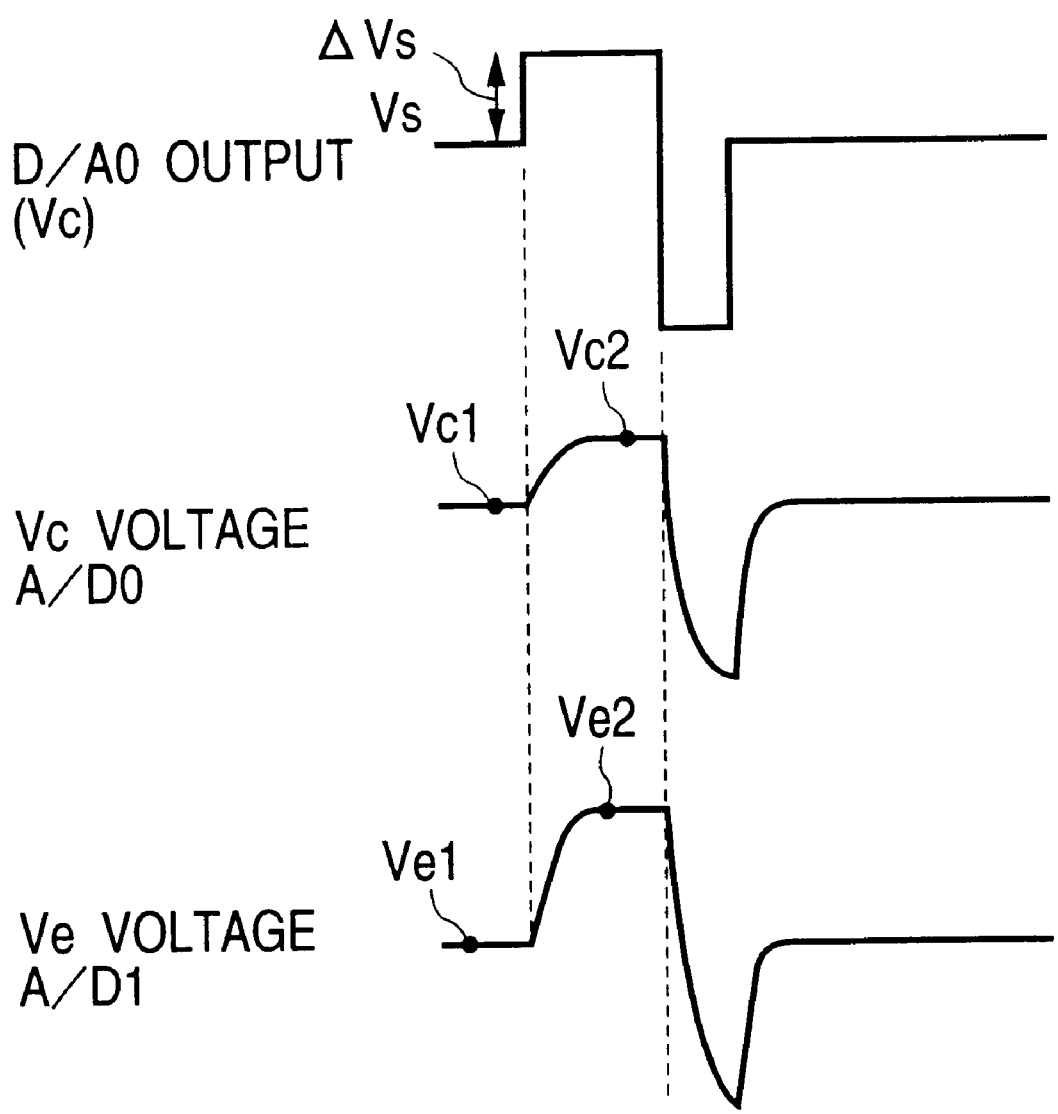
FIG. 13 is a waveform view showing signal changes during the impedance detection in accordance with the first embodiment of the present invention.

Next, the impedance detecting procedure for the sensor cell 120 performed in the step 350 shown in FIG. 9 will be explained with reference to the flowchart of FIG. 11 and the time chart shown in FIG. 13.

Figure 11:
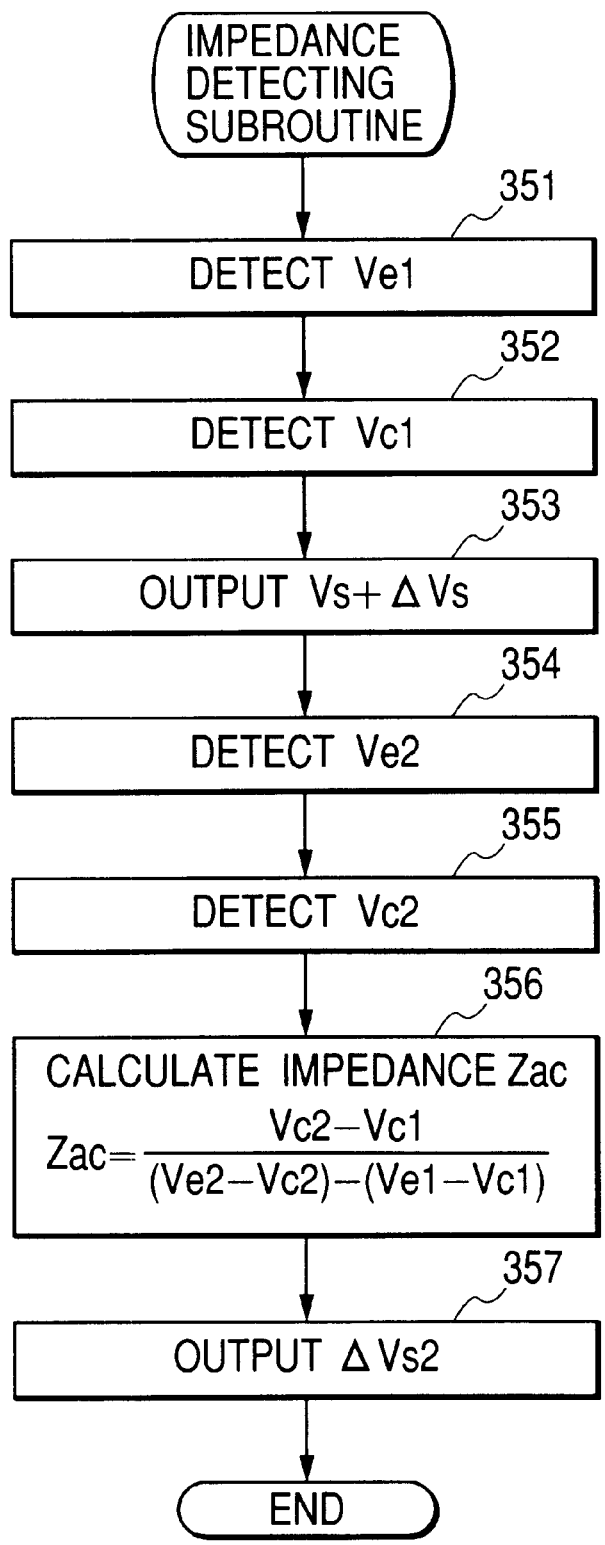
FIG. 11 is a flowchart showing an impedance detecting subroutine in accordance with the first embodiment of the present invention.

In FIG. 11, steps 351 and 352 detect terminal voltages Ve and Vc at the terminals of the current detecting resistor 222 through the convertors A/D1 and A/D0, respectively. The detected voltage values obtained in these steps 351 and 352 are referred to as current values Ve1 and Vc1 obtainable before the voltage changes. Then, step 353 outputs the voltage Vs+ΔVs through the converter D/A0, wherein Vs represents the present sensor cell application voltage and ΔVs represents a predetermined A.C. voltage. In this case, the applied voltages (i.e., Vc and Ve terminal voltages) vary like a sine wave in accordance with the time constant of LPF 230.

Thereafter, steps 354 and 355 detect terminal voltages Ve and Vc at the terminals of the current detecting resistor 222 through the convertors A/D1 and A/D0, respectively. The detected voltage values obtained in these steps 354 and 355 are referred to as current values Ve2 and Vc2 obtainable after the voltage changes. In practice, it is preferable to start the A/D reading operation of terminal voltages Ve2 and Vc2 approximately 25 μsec after the change of voltage.

Step 356 calculates the impedance Zac of sensor cell 120 based on the following equation.

$$Zac = \frac{Vc2 - Vc1}{(Ve2 - Vc2) - (Ve1 - Vc1)}$$

Finally, step 357 outputs ΔVs2 through the converter D/A0. The voltage ΔVs2 is applied to the sensor cell 120 to return the application voltage to the original voltage value Vs.

Figure 12:
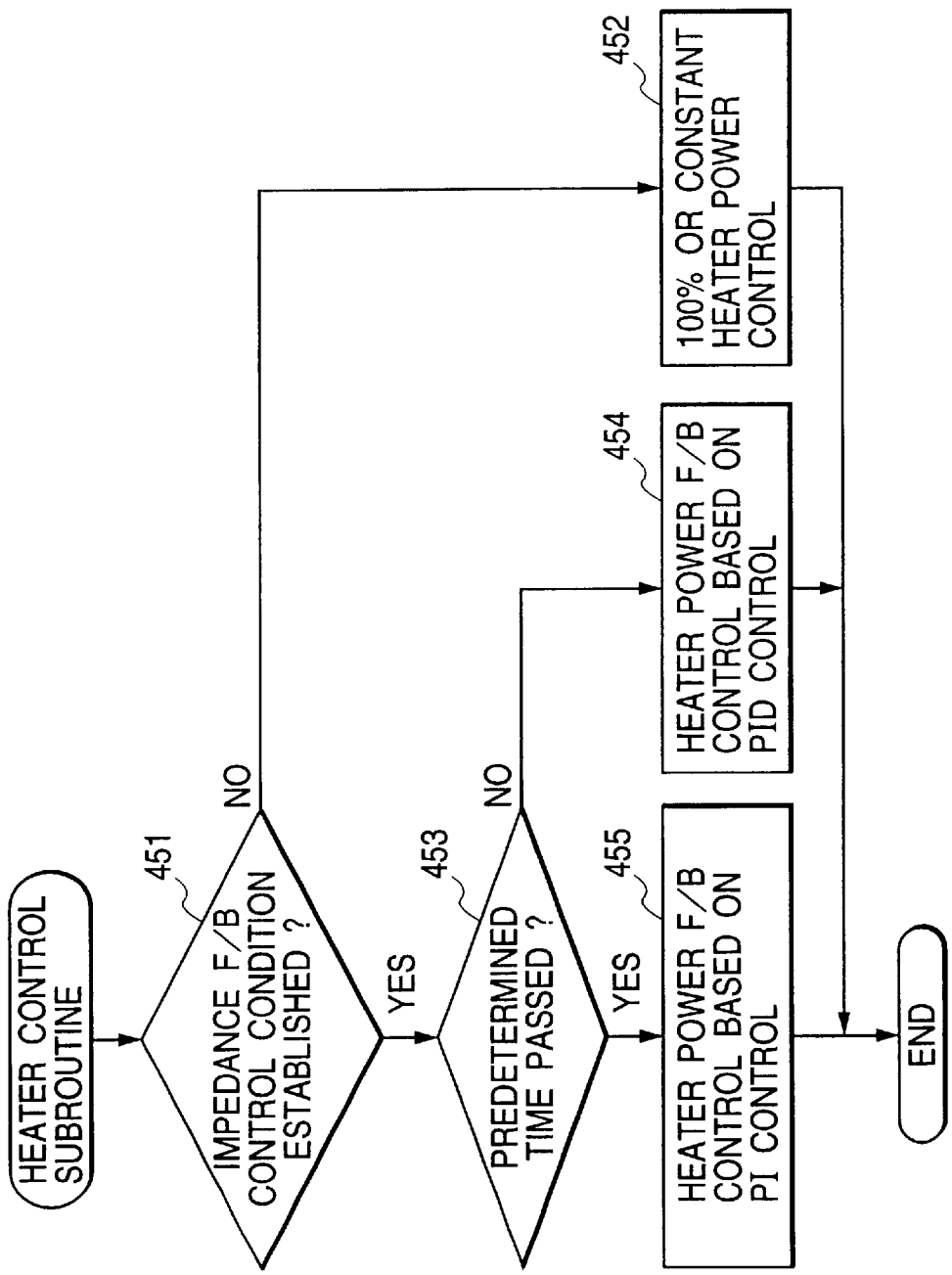
FIG. 12 is a flowchart showing a heater control subroutine in accordance with the first embodiment of the present invention.

Next, the heater control procedure will be explained with reference to the flowchart shown in FIG. 12. In FIG. 12, step 451 checks whether the impedance feedback control condition is established or not. For example, the impedance Zac of sensor cell 120 is usable to check the establishment of the impedance feedback control condition. When the Zac value reaches a predetermined active temperature (corresponding to cell temperature=650° C.), it is recognized that the impedance feedback control condition is established. When the judgement result is NO in step 451, the control flow proceeds to step 452 to perform the heater power control based on a 100% power supply. Alternatively, it is possible to perform a constant power control (e.g., 40 W) to reduce the thermal shock applied to each cell (sensor element).

For example, the PI (proportional-plus-integral) control can be used for performing the constant power control. More specifically, a proportional term GP and an integral term GI can be obtained in the following manner.

$GP=KP\cdot(W-WT)$ $GI=GI+KI\cdot(W-WT)$ where KP represents a proportional constant, KI represents an integral constant, W represents a detected heater power, and WT represents a target heater power. The control command value Duty, equal to "GP+GI", is used to control the heater power.

When the judgement result is YES in the step 451, it is then checked in step 453 whether a predetermined time (e.g., 20 seconds) has passed or not. When the judgement result is No in the step 453, the control flow proceeds to step 454 to perform the impedance feedback control based on a PID control technique. When the judgement result is YES in the step 453, the control flow proceeds to step 455 to perform the impedance feedback control based on a PI control technique. In short, the PID control is temporarily performed to improve the temperature convergence at a final stage of the heating operation of the gas concentration sensor 100. Thereafter, the PI control begins. However, it will be possible to omit the steps 453 and 454 if the temperature convergence is acceptable.

The impedance feedback control (i.e., PID control) in the step 454 is performed in the following manner. More specifically, a proportional term GP, an integral term GI, and a differential term GD can be obtained in the following manner.

$GP=KP\cdot(Zac-ZacT)$ $GI=GI+KI\cdot(Zac-ZacT)$ $GD=KD\cdot(Zac-ZacB)$ where Zac represents a detected impedance value of the sensor cell 120, ZacT represents a target impedance value of the sensor cell 120, and ZacB represents a previously detected impedance value of the sensor cell 120. A practical setting may be the proportional constant KP=1.8%, the integral constant KI=0.18%, and the differential constant KD=1.3%. The control command value Duty, equal to "GP+GI+GD", is used to control the heater power.

The impedance feedback control (i.e., PI control) in the step 455 is performed in the following manner. More specifically, a proportional term GP, and an integral term GI can be obtained in the following manner.

$GP=KP\cdot(Zac-ZacT)$ $GI=GI+KI\cdot(Zac-ZacT)$

The control command value Duty, equal to "GP+GI", is used to control the heater power.

The above-described first embodiment has the following effects.

As the heater power control is performed based on the impedance of the sensor cell 120 (i.e., second cell), the sensor cell 120 maintains a constant impedance. Accordingly, it becomes possible to prevent the NOx concentration sensing accuracy from being deteriorated due to undesirable temperature change of sensor cell 120 caused by the exhaust gas temperature change or the gas flow speed change. As a result, the purpose of the present invention, i.e., assuring the gas concentration sensing accuracy, can be attained. In this case, the temperature control of both cells 110 and 120 can be adequately performed by using only one heater 103.

Furthermore, as apparent from FIG. 2, the electric potential of the negative terminals of the pump cell 110 (i.e., first cell) and sensor cell 120 (i.e., second cell) are maintained at a level higher than 0V. According to this arrangement, negative current flows in each cell. Thus, it becomes possible to maintain the gas concentration in the porous diffusive layer 101 at a constant value regardless of lean or rich of the exhaust gas. For example, the oxygen concentration can be always maintained at a stoichiometric condition. As a result, the present invention enables the rich gas detection, expands the sensible range of the gas concentration, and improves the response of a gas concentration signal in a transient condition from a rich gas to a lean gas.

Figure 14:
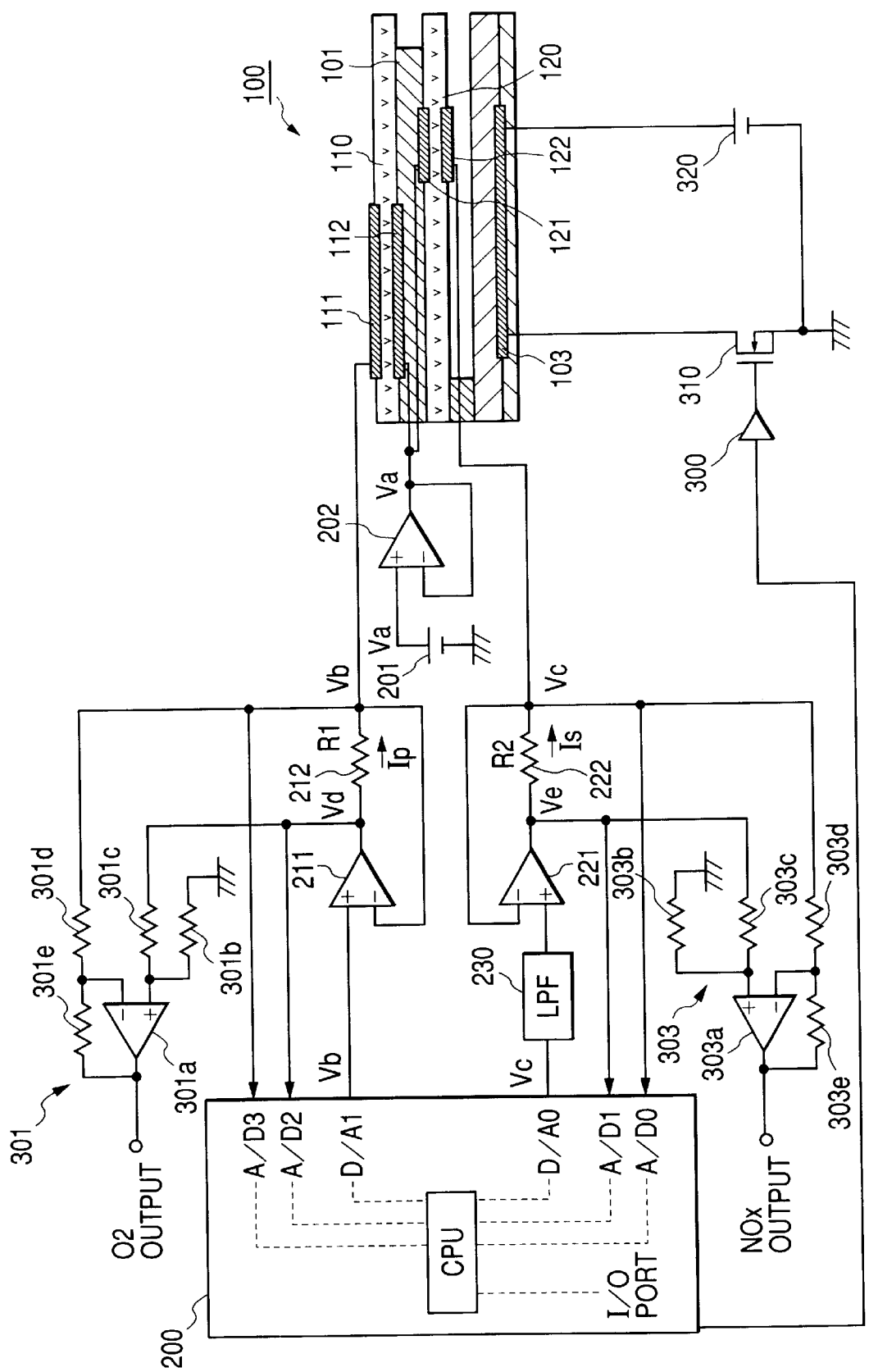
FIG. 14 is a diagram showing an overall arrangement of a modified gas concentration sensing apparatus in accordance with the first embodiment of the present invention.

FIG. 14 shows a modified arrangement of FIG. 2, according to which both the NOx concentration sensing means M1 and the oxygen concentration sensing means M3 are constituted by analog circuits for detecting analog gas concentration outputs. Namely, FIG. 14 is different from FIG. 2 in that an amplification circuit 301 is provided for differential amplifying the terminal voltages of the current detecting resistor 212 and an amplification circuit 303 is provided for differential amplifying the terminal voltages of the current detecting resistor 222. The amplification circuit 301, serving as an output section of the oxygen concentration sensing means M3, comprises an operational amplifier 301a and resistors 301b to 301e. The amplification circuit 303, serving as an output section of the NOx concentration sensing means M1, comprises an operational amplifier 303a and resistors 303b to 303e. The arrangement of FIG. 14 is advantageous in that the gas concentration sensing signal is continuous and, therefore, the gas concentration sensing signal can be obtained speedily.

Next, second to fifth embodiments of the present invention will be explained. In each embodiment, the components identical with those already disclosed in the first embodiment are denoted by the same reference numerals and will be explained simply hereinafter. Instead, the arrangements not disclosed in the first embodiment will be explained in greater detail.

Second Embodiment

When the gas concentration sensor 100 comprises a plurality of cells 110 and 120, respective cells have cell temperatures different from each other. In such a case, the overall sensor temperature distribution may not be ignorable. More specifically, the gas concentration sensor 100 has an extended heat-generating portion so as to realize a uniform heating distribution. However, there is a tendency that the sensor cell temperature is slightly lower than the pump cell temperature due to heat release or loss at the sensor installation portion near the sensor cell. For example, even when the engine is in an idling condition or when the exhaust gas temperature or the gas flow speed is constant, the temperature near the sensor cell electrode is approximately 760° C. while the temperature near the pump cell electrode is approximately 800° C., causing a temperature difference of approximately 40° C.

Figure 15:
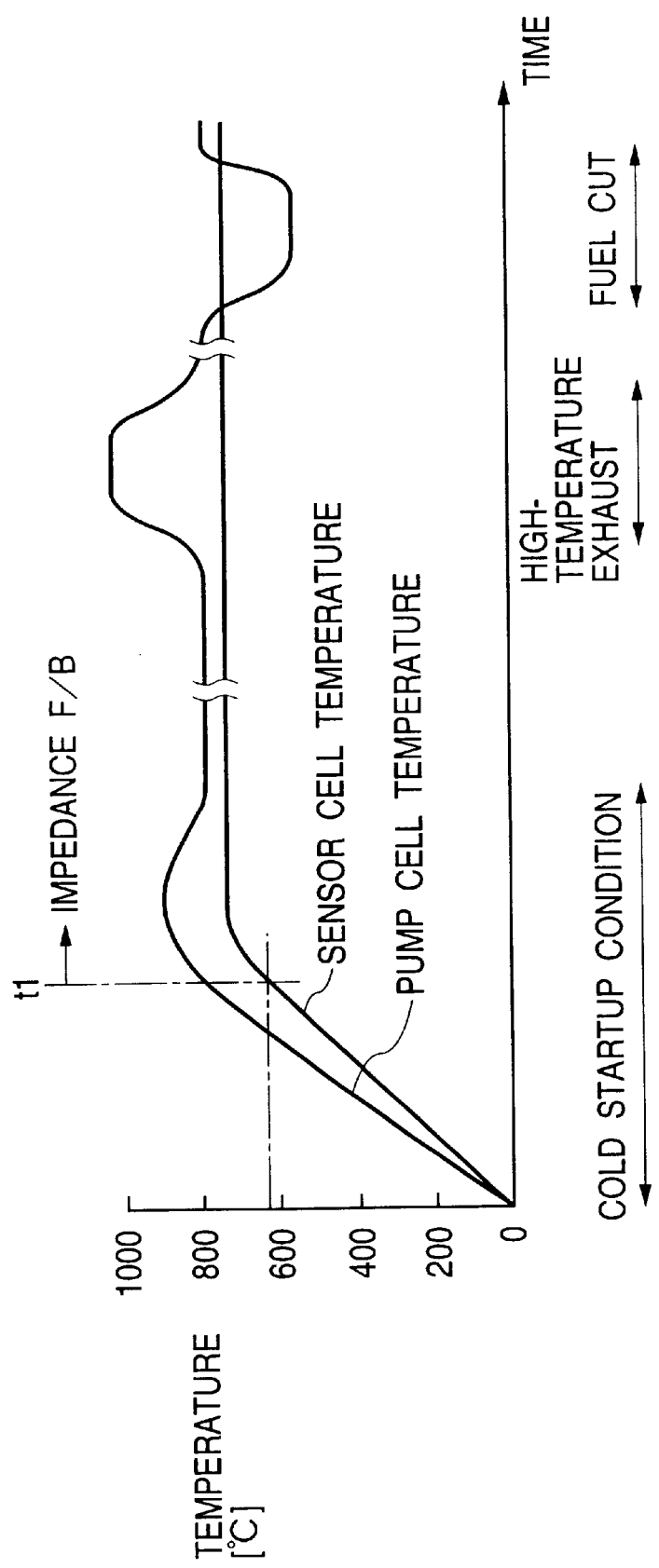
FIG. 15 is a time chart showing the transition of the cell temperature starting from an engine startup condition.

In an engine cold startup operation, the pump cell temperature increase is faster than the sensor cell temperature increase. The temperature difference between the pump cell 110 and the sensor cell 120 becomes larger compared with the equilibrium condition. If the feedback control is performed in this condition for equalizing the sensor cell impedance to a target value, the pump cell temperature will excessively increase due to an overshoot shown in FIG. 15. The excessive temperature increase possibly deteriorates the pump cell 110. In FIG. 15, a 100% power control or a constant power control is performed before time t1. Then, an impedance feedback control is performed after the time t1 to equalize the sensor cell impedance to a constant value.

When the exhaust gas temperature is very high, or when the exhaust gas temperature is low due to, for example, a long lasting fuel cut operation, the pump cell temperature tends to increase or decrease excessively because the pump cell 110 is exposed to the exhaust gas. This possibly changes the temperature distribution of the gas concentration sensor 100 and worsens the function of the gas concentration sensor 100.

To solve this problem, the second embodiment detects a pump cell impedance in addition to the sensor cell impedance. In the following description, "Zs" represents the impedance of sensor cell 120 and "Zp" represents the impedance of pump cell 110. The heater power is controlled by selectively performing a feedback control based on a detected Zs value and a feedback control based on a detected Zp value.

Figure 16:
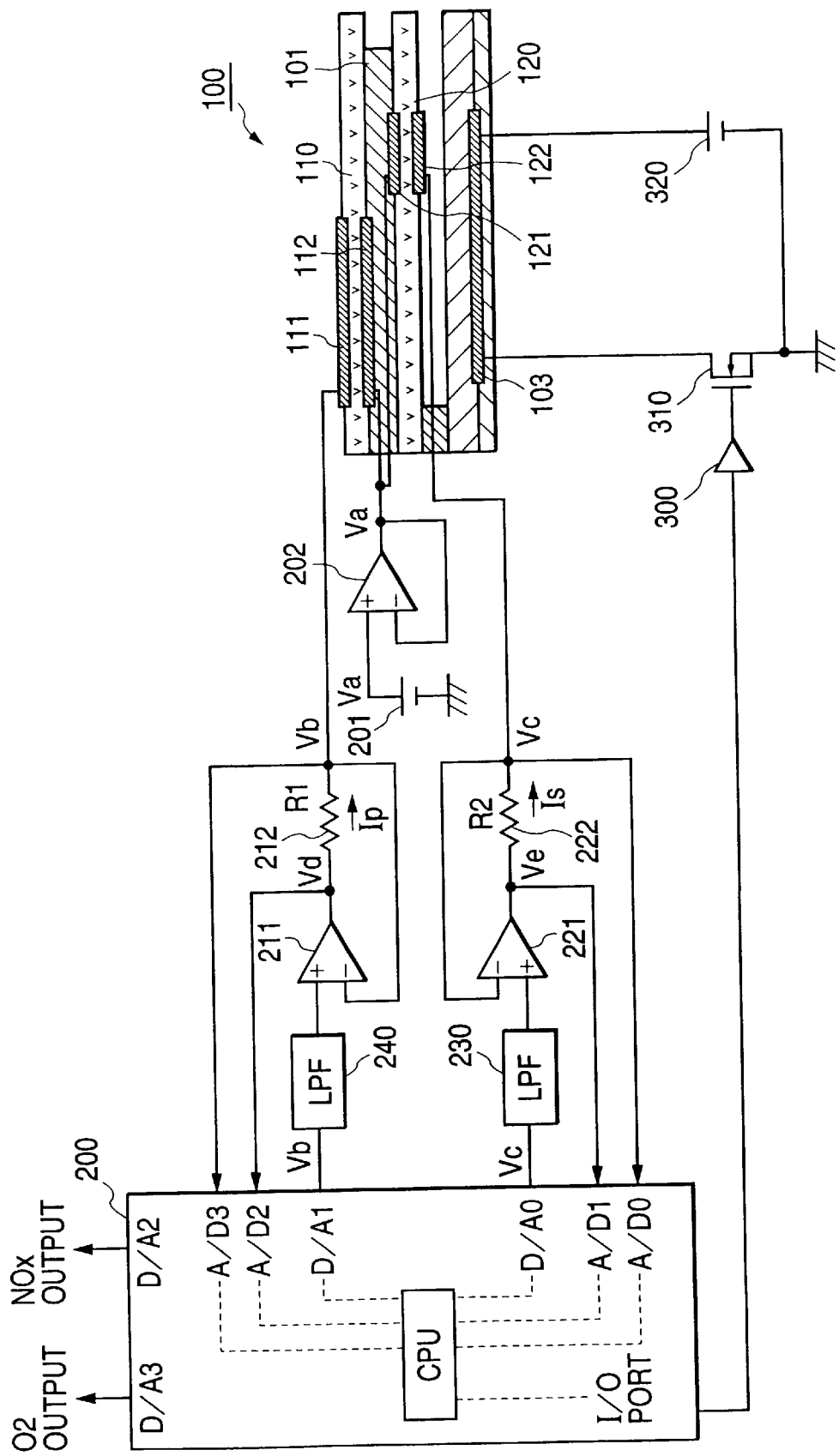
FIG. 16 is a diagram showing an overall arrangement of a gas concentration sensing apparatus in accordance with a second embodiment of the present invention.

FIG. 16 shows an arrangement of a gas concentration sensing apparatus in accordance with the second embodiment. The arrangement shown in FIG. 16 is different from the arrangement shown in FIG. 2 in that an LPF 240 is added for smoothing or relaxing an A.C. change of the applied voltage in the detection of the pump cell impedance. The control circuit 200 detects the impedance of pump cell 110 based on the voltage values Vd and Vb detected via the converters A/D2 and A/D3 in addition to the impedance detection of the sensor cell 120.

More specifically, the control circuit 200 instantaneously changes the pump cell voltage which is outputted via the converter D/A1. The pump cell voltage is then modified into a sine wave form through the LPF 240 and applied to the pump cell 110. A desirable A.C. voltage frequency is 10 kHz or above. The time constant of LPF 240 is set to approximately 5 μs. The converters A/D2 and A/D3 detect the changes of terminal voltages Vd and Vb at the both ends of current detecting resistor 212, respectively. The A.C. impedance of pump cell 110 can be calculated based on the voltage change amount and the current change amount thus obtained.

The impedance detecting procedure for the pump cell 110 is fundamentally identical with the processing procedure shown in FIG. 11 and, therefore, will not be disclosed and explained specially. The terminal voltages Vd and Vb of the current detecting resistor 212, obtainable before and after the voltage changes, are detected through the convertors A/D2 and A/D3, respectively. The impedance Zp of pump cell 110 is calculated based on the voltage values thus detected. It is preferable to execute the above-described Zp value detecting processing immediately after the step 230, i.e., the sensor cell impedance detecting processing, in the main routine shown in FIG. 9.

Figure 17:
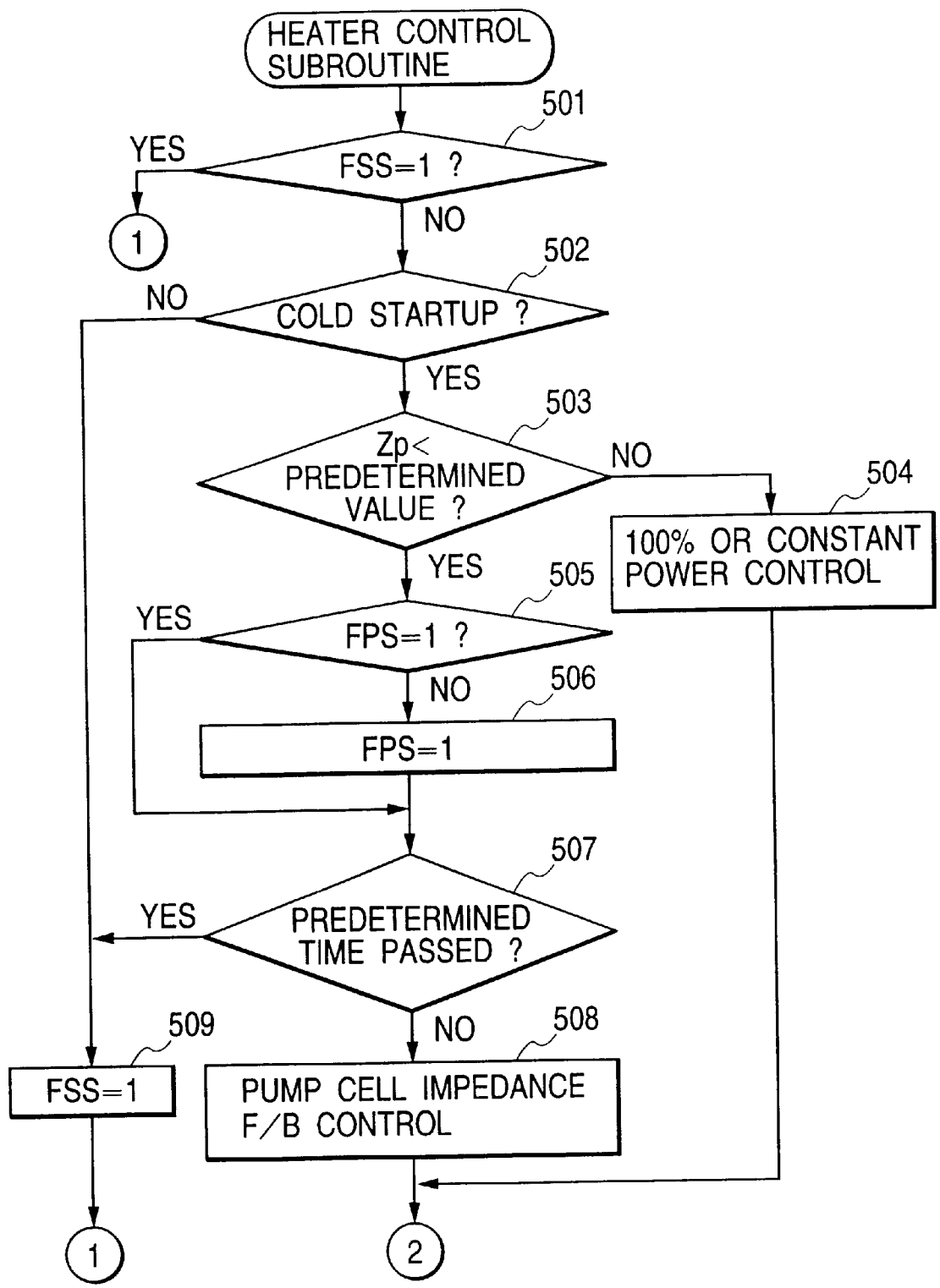
FIG. 17 is a flowchart showing a front half of a heater control subroutine in accordance with the second embodiment of the present invention.
Figure 18:
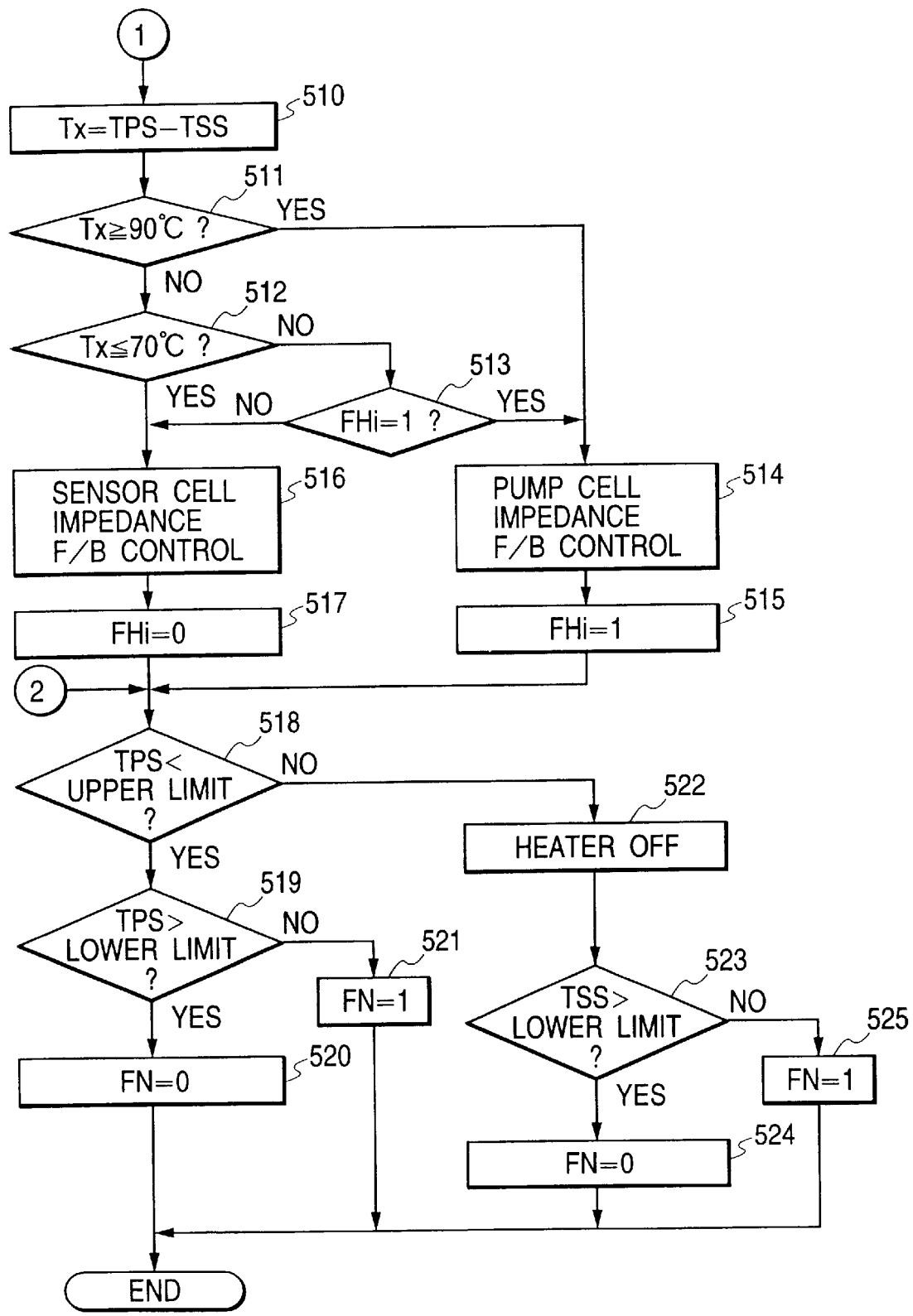
FIG. 18 is a flowchart showing a second half of the heater control subroutine in accordance with the second embodiment of the present invention.

FIGS. 17 and 18 are a flowchart showing a heater control subroutine in accordance with the second embodiment. In other words, this routine is replaced for the routine shown in FIG. 12. Hereinafter, the heater control procedure shown in FIGS. 17 and 18 will be explained with reference to time charts shown in FIGS. 19 and 20.

In FIG. 17, step 501 checks whether a sensor cell feedback flag FSS is 1 or not. The sensor cell feedback flag FSS indicates that the impedance feedback control for the sensor cell 120 is presently performed. Thus, FSS is "0" in a condition (i.e., in an initial condition) where the feedback control is not executed. FSS is turned to "1" after the feedback control is started.

For example, when FSS is 0 (i.e., FSS=0) in the engine startup condition, the control flow proceeds to step 502. The step 502 checks whether the present engine operation is in a cold startup condition or not. This judgement can be done based on the impedance Zp of the pump cell 110. When the impedance Zp is equal to or larger than a predetermined value (e.g., cell temperature=200° C.), the judgement result of step 502 becomes YES. Alternatively, it is possible to perform the step 502 judgement based on the engine operating conditions.

When the judgement result is YES in the step 502, the control flow proceeds to step 503. The step 503 checks whether the pump cell impedance Zp is smaller than a predetermined value (e.g., a value equivalent to the cell temperature=650° C.). When the judgement result is NO in the step 503, the control flow proceeds to step 504 to execute the 100% power control or the constant power control.

When the judgement result is YES in the step 503, the control flow proceeds to step 505 to check whether a pump cell feedback flag FPS is 1 or not. When the pump cell feedback flag FPS is not 1, the control flow proceeds to step 506 to set the flag FPS to 1 (FPS=1). The pump cell feedback flag FPS indicates the execution of the pump cell impedance feedback control in the temperature increasing process starting from the cold startup condition.

Thereafter, step 507 checks whether a predetermined time (e.g., 30 seconds) has passed after the FPS is turned to 1. When the judgement result is NO in the step 507, the control flow proceeds to step 508. The step 508 executes the impedance feedback control for the pump cell 110. Namely, the heater power control is performed based on a PI or PID control technique. After finishing the step 504 or 508, the control flow proceeds to a later-described step 518 shown in FIG. 18. When the judgement result is YES in the step 507, the control flow proceeds to step 509 to set the sensor cell feedback flag FSS to 1. Then, the control flow proceeds to step 510 shown in FIG. 18.

On the other hand, when the judgement result is YES in the step 501, the control flow directly proceeds to the step 510. When the judgement result is NO in the step 502, the control flow proceeds to the step 509 to set the sensor cell feedback flag FSS to 1. Then, the control flow proceeds to the step 510 of FIG. 18.

Figure 19:
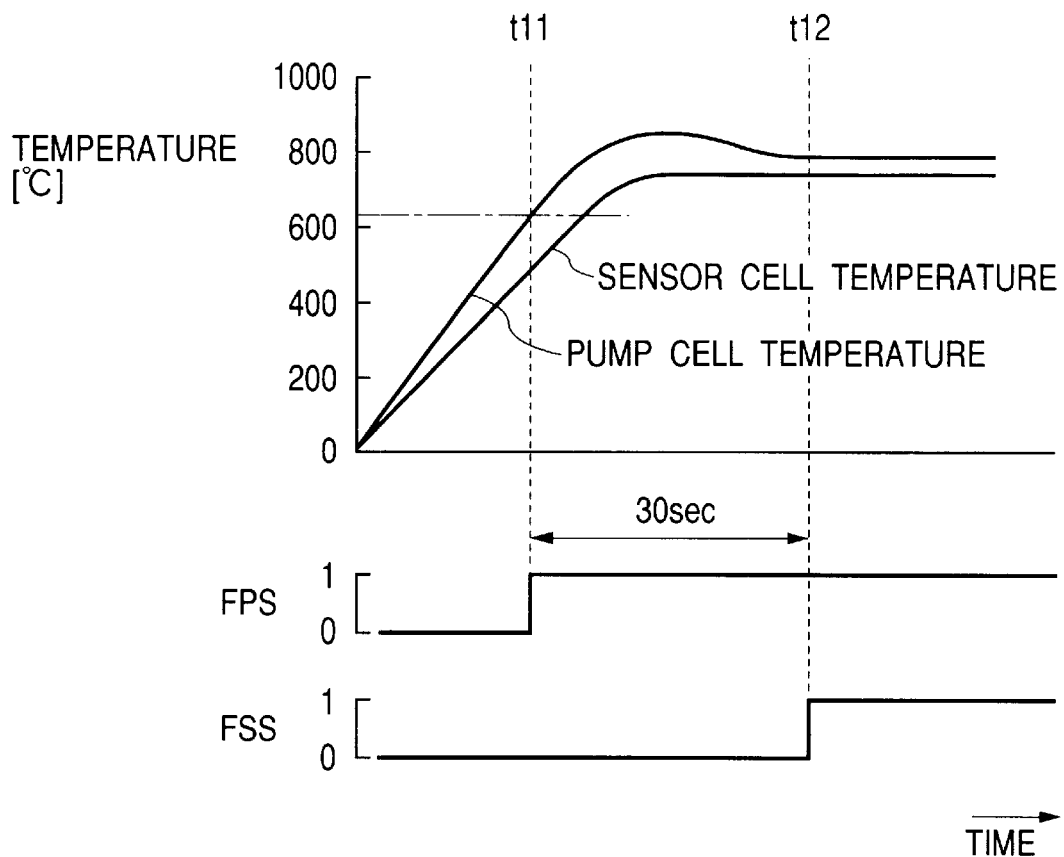
FIG. 19 is a time chart showing the transition of the cell temperature in the engine startup condition in accordance with the second embodiment of the present invention.

According to the above-described processing procedure, as shown in the time chart of FIG. 19, the temperatures of cells 110 and 120 continuously increase after starting the engine operation in a cold condition. The pump cell temperature increases to 650° C. at the time t11. At the time t11, the pump cell feedback flag FPS is turned to 1 and the impedance feedback control for the pump cell 110 is started (refer to steps 506 and 508 in FIG. 17). After the time t11, the pump cell temperature reaches the target value under the impedance feedback control for the pump cell 110. Thus, it becomes possible to suppress the overshoot phenomenon shown in FIG. 15. At the time t12, i.e., when the predetermined time (30 seconds) has passed after the commencement of the impedance feedback control of the pump cell 110, the sensor cell feedback flag FSS is turned to 1 (refer to step 509 in FIG. 17).

In FIG. 18, the step 510 obtains a temperature difference Tx between the pump cell temperature TPS and the sensor cell temperature TSS (Tx=TPS−TSS). The pump cell temperature TPS and the sensor cell temperature TSS are indirectly obtainable from the corresponding cell impedances Zp and Zs, respectively.

Subsequently, steps 511 to 517 selectively execute the "impedance feedback control of pump cell 110" and the "impedance feedback control of sensor cell 120" in accordance with the temperature difference Tx. More specifically, step 511 checks whether the temperature difference Tx is equal to or larger than 90° C. (i.e., Tx≧90°). Step 512 checks whether the temperature difference Tx is equal to or smaller than 70° C. (i.e., Tx≦70°). When the judgement result is YES in the step 511(i.e., Tx≧90°), the control flow proceeds to step 514. The step 514 performs the impedance feedback control of the pump cell 110. Next step 515 sets a temperature difference flag FHi to 1 (i.e., FHi=1).

When the judgement result is YES in the step 512(i.e., Tx≦70°), the control flow proceeds to step 516. The step 516 performs the impedance feedback control of the sensor cell 120. Next step 517 resets the temperature difference flag FHi to 0 (i.e., FHi=0). When the judgement result is NO in the steps 511 and 512 (i.e., 70° C.<Tx<90° C.), the control flow proceeds to step 513 to selectively perform the steps 514 and 516 in accordance with the temperature difference flag FHi.

Figure 20:
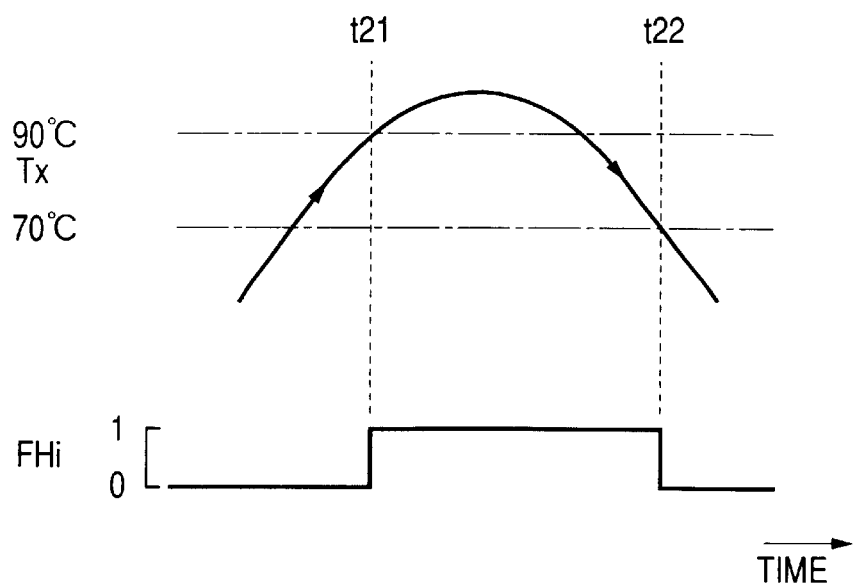
FIG. 20 is a time chart illustrating the switching of an impedance feedback control in accordance with the second embodiment of the present invention.

According to the processing procedure of the above-described steps 511 to 517, as shown in the time chart of FIG. 20, the temperature difference flag FHi is held to 0 (initial value) until the temperature difference Tx reaches 90° C. (i.e., before the time t21). In this condition, the impedance feedback control for the sensor cell 120 is performed (refer to step 516 in FIG. 18). When the temperature difference Tx has just reached 90° C. (i.e., at the time t21), the temperature difference flag FHi is turned to 1. The impedance feedback control for the pump cell 110 is performed (refer to step 514 in FIG. 18). Thereafter, when the temperature difference Tx reduces to 70° C. (i.e., at the time t22), the temperature difference flag FHi is turned to 0 to resume the impedance feedback control for the sensor cell 120 (refer to step 516 in FIG. 18).

In short, when the exhaust gas temperature is stable, the temperature difference Tx is relatively small. In such a condition, the impedance feedback control for the sensor cell 120 is performed. The exhaust gas temperature may increase temporarily. The pump cell temperature is sensitively influenced by the increased exhaust gas temperature. Thus, the temperature difference Tx becomes relatively large. The impedance feedback control for the pump cell 110 is performed. According to the processing procedure of the steps 511 to 517, a hysteresis is provided in the judgement of the temperature difference Tx. This is effective to eliminate the hunting phenomenon in the feedback control.

Returning to the processing procedure of FIG. 18, steps 518 to 525 perform the cell temperature guard processing. More specifically, step 518 checks whether the pump cell temperature TPS is lower than a predetermined upper limit (e.g., 900° C.). The pump cell temperature TPS is indirectly obtainable from the pump cell impedance Zp. When the judgement result is YES in the step 518 (i.e., TPS<upper limit), the control flow proceeds to step 519. The step 519 further checks whether the pump cell temperature TPS is higher than a predetermined lower limit (e.g., 650° C.). When the judgement result is YES in the step 519 (i.e., TPS>lower limit), the control flow proceeds step 520. Step 520 resets a sensor inactive flag FN to 0. When the judgement result is NO in the step 519 (i.e., TPS≦lower limit), the control flow proceeds step 521. Step 521 sets the sensor inactive flag FN to 1. In this case, the reset condition "FN=0" indicates that the pump cell temperature is so low that the gas concentration sensor 100 cannot operate normally.

When the judgement result is NO (i.e., TPS≦upper limit), the control flow proceeds to step 522. The step 522 forcibly stops the heater power supply to prevent the heater from being thermally damaged. Next step 523 checks whether the sensor cell temperature TSS is higher than a predetermined lower limit (e.g., 650° C.).The sensor cell temperature TSS is indirectly obtainable from the sensor cell impedance Zs. When the judgement result is YES in the step 523 (i.e., TSS>lower limit), the control flow proceeds step 524. Step 524 resets the sensor inactive flag FN to 0. When the judgement result is NO in the step 523 (i.e., TSS≦lower limit), the control flow proceeds step 525. Step 525 sets the sensor inactive flag FN to 1. Needless to say, the above-described judgements in the steps 518, 519, and 523 can be performed by using the impedance Zp or Zs.

Figure 21:
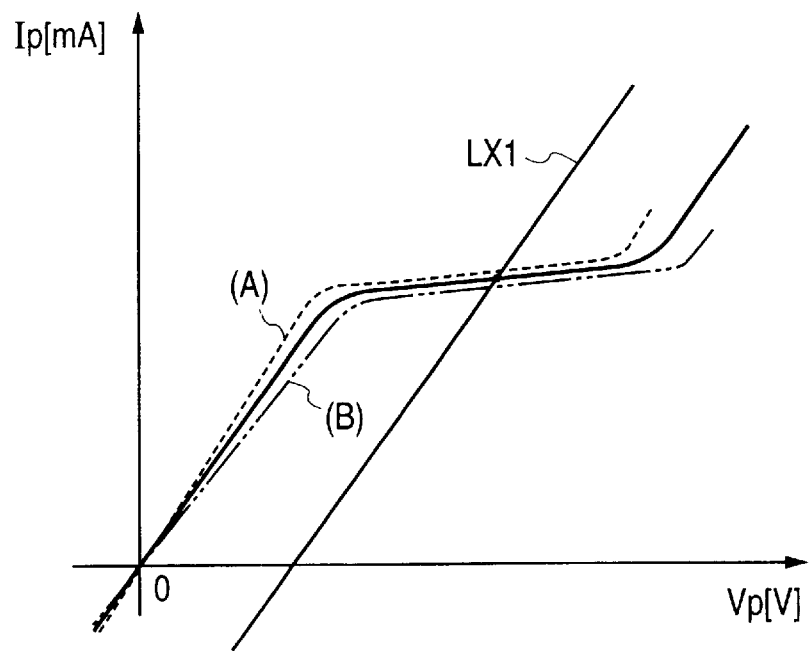
FIG. 21 is a V-I characteristic graph showing changes of the pump cell characteristics responsive to the temperature change.

Meanwhile, in the pump cell characteristics, the inclination representing the D.C. resistance component varies in response to the temperature distribution change caused by the increased exhaust gas temperature. More specifically, as shown in FIG. 21, in the V-I characteristics, the inclination representing the D.C. resistance component increases with increasing pump cell temperature (refer to (A)) and decreases with decreasing pump cell temperature (refer to (B)). The limit-current sensible region is slightly ascendent right relative to the V axis. The voltage application point for determining the pump cell voltage is usually set to a center of the limit-current sensible region. Thus, the voltage application point shifts left in the inclination change of line (A), and shifts right in the inclination change of line (B).

Accordingly, the present invention provides new application voltage lines LXa, LXb and LXc in addition to the standard or basic application voltage line LX1. One of the plurality of application voltage lines LX1, LXa, LXb and LXc is selectively used in accordance with the impedance value of the pump cell 110. When the pump cell temperature is high, i.e., when the inclination representing the D.C. resistance component increases, it is preferable to select the application voltage line LXa. When the pump cell temperature is low, i.e., when the inclination representing the D.C. resistance component decreases, it is preferable to select either the application voltage line LXb or LXc. Such a selection of an optimum application voltage line from a plurality of application voltage lines makes it possible to appropriately set the application voltage even when the voltage application point for determining the pump cell voltage shifts right or left.

Figure 22:
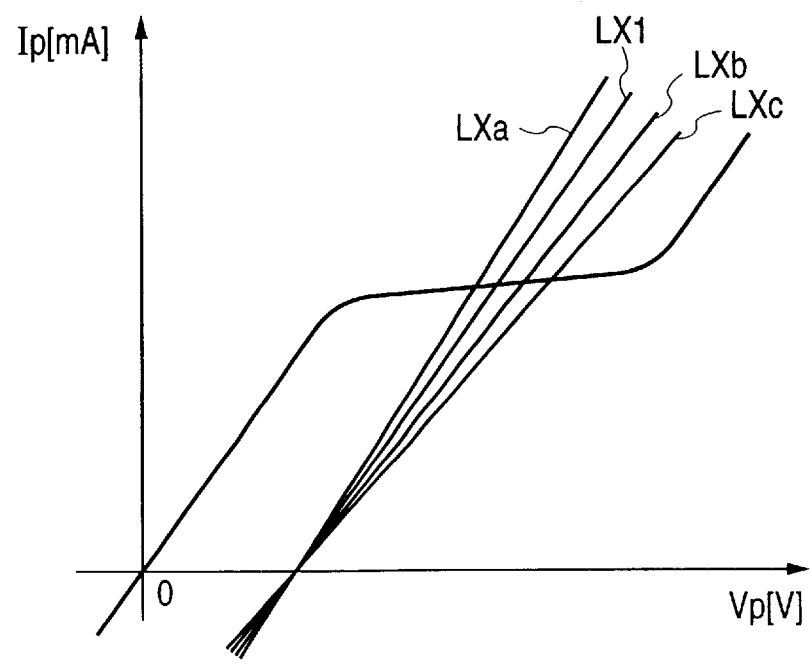
FIG. 22 is a V-I characteristic graph including a plurality of application voltage lines in accordance with the second embodiment of the present invention.
Figure 23:
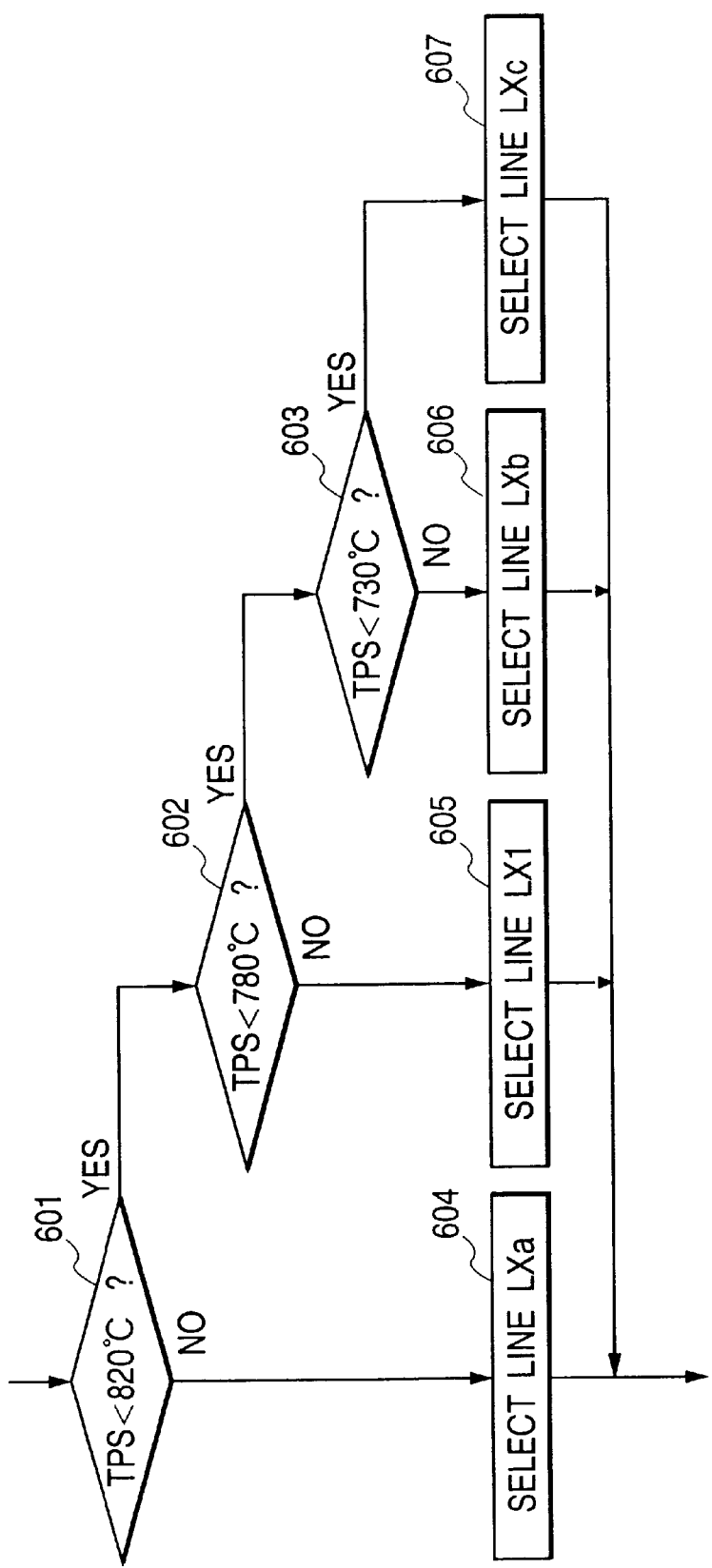
FIG. 23 is a flowchart showing part of the application voltage control in accordance with the second embodiment of the present invention.

FIG. 23 is a flowchart showing a processing procedure for varying the pump cell application voltage by selectively using the plurality of application voltage lines LX1, LXa, LXb, and LXc shown in FIG. 22. For example, this routine can be inserted between the steps 204 and 205 of FIG. 10.

In FIG. 23, step 601 checks whether the pump cell temperature TPS is lower than a first reference value (e.g., 820° C.). Step 602 checks whether the pump cell temperature TPS is lower than a second reference value (e.g., 780° C.). Step 603 checks whether the pump cell temperature TPS is lower than a third reference value (e.g., 730° C.). The pump cell temperature TPS is indirectly obtainable from the pump cell impedance Zp.

When the judgement result is NO in the step 601, the control flow proceeds to step 604 to select the application voltage line LXa of FIG. 22.

When the judgement result is NO in the step 602, the control flow proceeds to step 605 to select the application voltage line LX1 of FIG. 22.

When the judgement result is NO in the step 603, the control flow proceeds to step 606 to select the application voltage line LXb of FIG. 22.

When the judgement result is YES in the step 603, the control flow proceeds to step 607 to select the application voltage line LXc of FIG. 22.

In other words, the application voltage line LXa is selected when TPS≧820° C. The application voltage line LX1 is selected when 780° C.≦TPS<820° C. The application voltage line LXb is selected when 730°C.≦TPS<780° C. And, the application voltage line LXc is selected when TPS<730° C. Needless to say, the above-described judgements in the steps 601 to 603 can be performed by using the impedance Zp.

According to the second embodiment, the steps 503, 511 to 513 of FIGS. 17 and 18 cooperatively serve as a judging means of the present invention. And, the steps 508, 514 and 516 of FIGS. 17 and 18 cooperatively serve as a power control means of the present invention.

The above-described second embodiment makes it possible to adequately maintain the NOx concentration sensing accuracy regardless of the exhaust gas temperature or the gas flow speed change in the same manner as in the above-described first embodiment. Furthermore, the second embodiment brings the following effects. Namely, the second embodiment judges temperature conditions relating to the activation of respective cells 110 and 120 (refer to FIGS. 17 and 18). Then, the second embodiment selectively performs the impedance feedback control of the pump cell 110 and the impedance feedback control of the sensor cell 120 in accordance with the judgement result. Thus, the gas concentration sensing accuracy is not deteriorated even when the temperature characteristics of each cell is differentiated due to the sensor structure. As a result, it becomes possible to adequately maintain the gas concentration sensing accuracy regardless of the fluctuation in the cell temperature distribution.

In practice, in the beginning of the cold startup operation, the impedance feedback control is performed for the high-temperature cell among the plurality of cells 110 and 120. According to this embodiment, the impedance feedback control for the pump cell 110 begins early. The impedance feedback control for the sensor cell 120 starts later. Furthermore, when the temperature difference between cells is relatively large, the impedance feedback control is performed for the high-temperature cell. According to this embodiment, the impedance feedback control for the pump cell 110 is performed when the cell temperature difference is relatively large. The impedance feedback control for the sensor cell 120 is performed when the cell temperature difference is relatively small. Accordingly, when the exhaust gas temperature is stable, the impedance feedback control for the sensor cell 120 is performed. When the exhaust gas temperature increases temporarily, the impedance feedback control is performed for the cell which is most sensitively influenced by the exhaust gas temperature increase. With the above arrangement, it becomes possible to adequately maintain the gas concentration sensing accuracy regardless of the fluctuation in the cell temperature distribution.

Furthermore, the second embodiment guards the pump cell temperature and the sensor cell temperature by providing the predetermined upper and lower values. Thus, it becomes possible to solve the problems such as the sensor deterioration caused by the excessive temperature increase and the sensing performance decline derived from the temperature decrease.

Furthermore, the second embodiment controls the voltage applied to the pump cell 110 in accordance with the impedance of this pump cell 110. This is advantageous in that the pump cell voltage can be adequately managed and the oxygen concentration accuracy can be appropriately maintained. The improvement in the oxygen concentration sensing accuracy brings the improvement in the NOx concentration sensing accuracy.

Third Embodiment

When the impedance detection for the pump cell 110 and the sensor cell 120 is performed based on the sweep method as explained in the second embodiment, the voltage applied to each cell for detecting the impedance has an A.C. component. In this case, there is a current interference problem that the A.C. current change of one cell may give adverse influence to the other cell whose impedance is not detected. For example, when the pump cell impedance is detected, a current flows in the sensor cell in synchronism with the application of an A.C. voltage to the pump cell. The sensor cell current Is varies unwantedly (by several μA). In the same manner, when the sensor cell impedance is detected, a current flows in the pump cell in synchronism with the application of an A.C. voltage to the sensor cell. The pump cell current Ip varies unwantedly (by several $\mu$A).

The third embodiment of the present invention eliminates such an adverse interference during the impedance detection by providing a sample hold circuit in an output path of the oxygen concentration or NOx concentration signal.

Figure 24:
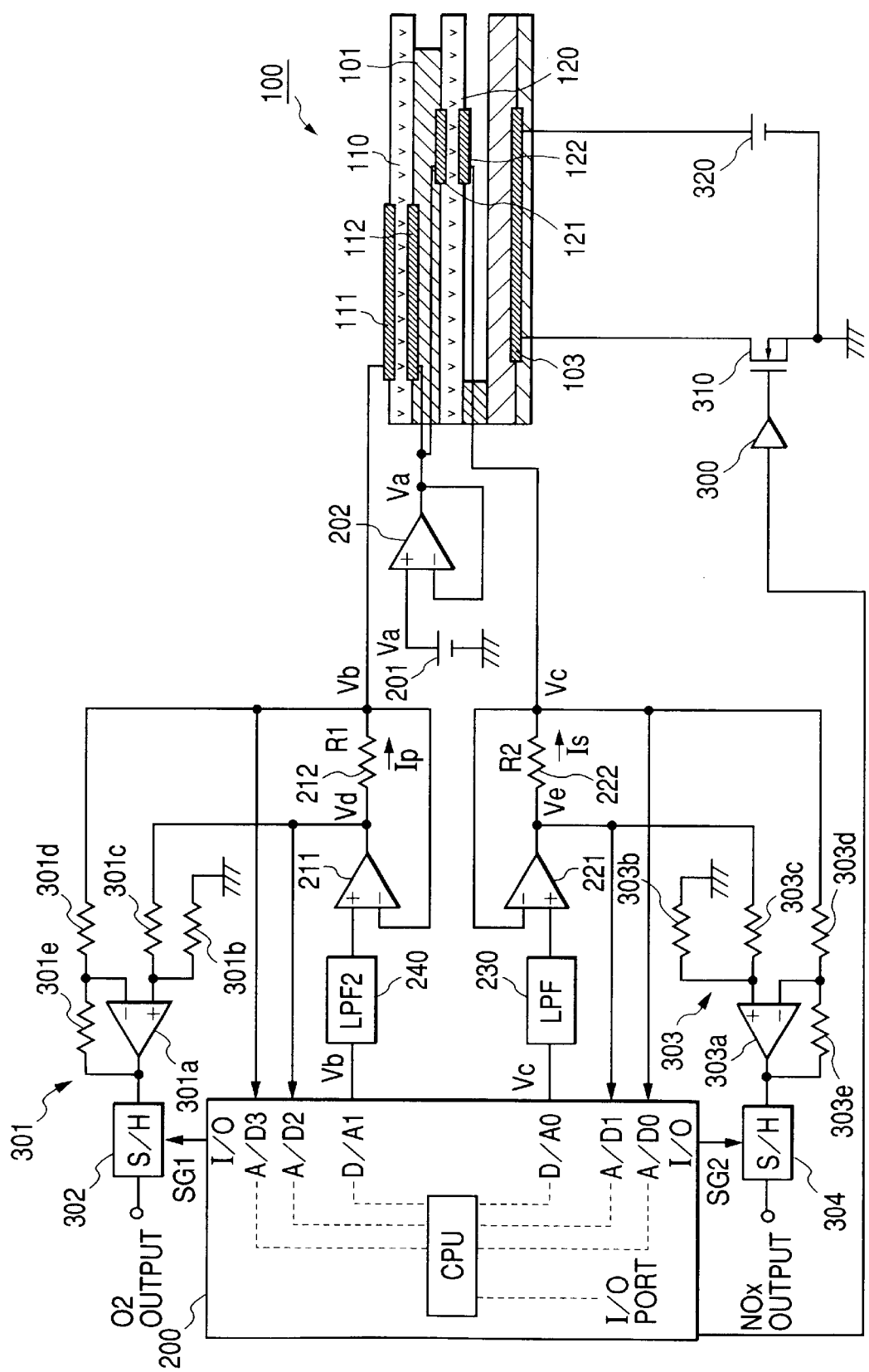
FIG. 24 is a diagram showing an overall arrangement of a gas concentration sensing apparatus in accordance with a third embodiment of the present invention.

FIG. 24 shows a detailed arrangement of a gas concentration sensing apparatus in accordance with the third embodiment. FIG. 24 is different from FIG. 16 in that the amplification circuit 301, consisting of the operational amplifier 301a and the resistors 301b to 301e, is connected to both ends of the current detecting resistor 212, and also in that a sample hold circuit 302 is connected to the output terminal of the amplification circuit 301. The sample hold circuit 302 samples the pump cell current Ip representing a detected oxygen concentration, and successively renews the sample value in a predetermined gate-on period during which a signal SG1 is turned on.

Furthermore, the amplification circuit 303, consisting of the operational amplifier 303a and the resistors 303b to 303e, is connected to both ends of the current detecting resistor 222. And, a sample hold circuit 304 is connected to the output terminal of the amplification circuit 303. The sample hold circuit 304 samples the sensor cell current Is representing a detected NOx concentration, and successively renews the sample value in a predetermined gate-on period during which a signal SG2 is turned on.

Figure 25:
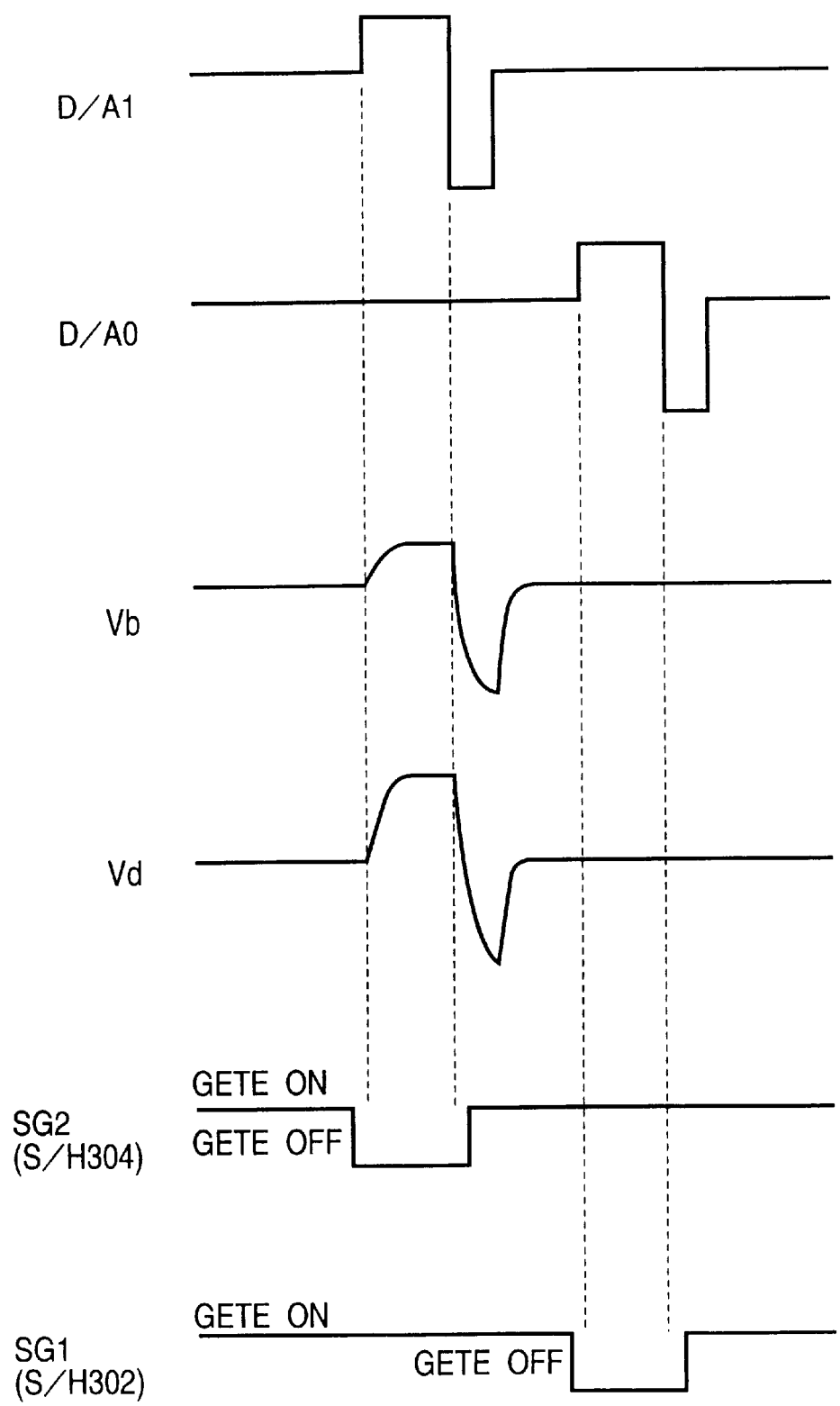
FIG. 25 is a time chart showing signal waveforms in accordance with the third embodiment of the present invention.
Figure 26:
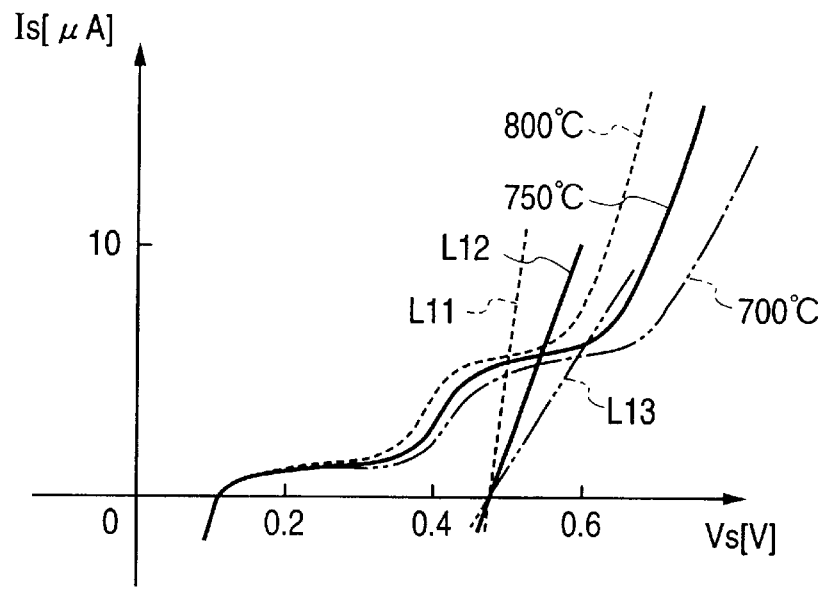
FIG. 26 is a V-I characteristic graph showing changes of the sensor cell characteristics responsive to the temperature change.

According to the above-described arrangement, as shown in the time chart of FIG. 25, the control circuit 200 produces a command signal Vb as a D/A1 signal to detect the pump cell impedance. During the detection of the pump cell impedance, the control circuit 200 produces a SG2 signal to hold the sample hold circuit 304 provided for the sensor cell 120. As a result, the NOx concentration signal corresponding to the sensor cell current Is held at a value detected immediately before the gate off timing. In other words, it becomes possible to prevent the sensor output from fluctuating due to the cell interference.

In the same manner, the control circuit 200 produces a command signal Vc as a D/A0 signal to detect the sensor cell impedance. During the detection of the sensor cell impedance, the control circuit 200 produces a SG1 signal to hold the sample hold circuit 302 provided for the pump cell 110. As a result, the oxygen concentration signal corresponding to the pump cell current Ip is held at a value detected immediately before the gate off timing. Thus, it becomes possible to prevent the sensor output from fluctuating due to the cell interference.

Although not shown in the drawing, it is possible to temporarily stop the renewal of the gas concentration signal of a cell whose impedance should be detected. Namely, the gas concentration signal is held at a value immediately before starting the impedance detection. This makes it possible to prevent any sensor output (any gas concentration) from fluctuating.

The above-described third embodiment newly brings the following effects. Namely, according to the system temporarily changing the voltage applied to each cell for detecting the impedance of the pump cell 110 or the sensor cell 120, the current interference responsive to the voltage change occurs between the cells. Thus, the gas concentration signal may vary unwantedly. To solve such problems, the third embodiment provides the sample hold circuits 302 and 304 to hold the gas concentration signals at the latest values during the impedance detection.

Fourth Embodiment

The fourth embodiment detects both the pump cell impedance and the sensor cell impedance and performs the impedance feedback control of heater 103 based on a sum (or an average) of the detected impedance values.

For example, when a target pump cell temperature is 800° C. and a target sensor cell temperature is 760° C., a target value of the impedance feedback control is a sum of them (=1,560° C.). When the sensor cell temperature is controlled to a target value (i.e., 760° C.), the temperature distribution of gas concentration sensor 100 may vary. When the pump cell temperature increases to 910° C. which is 110° C. higher than the target value, the cell temperature difference becomes "+150° C.". In this case, the pump cell 110 is in an excessively heated condition. Hence, the heater power control is performed in such a manner that the sum of cell temperatures is equalized to the target value (1,560° C.). In each cell, the temperature decreases by an amount of 55° C. The sensor cell temperature becomes 705° C. and the pump cell temperature becomes 855° C. Thus, the excessively heated condition of the pump cell 110 is eliminated through such a heater control.

On the other hand, when the sensor cell temperature is controlled to the target value (i.e., 760° C.), the temperature distribution of gas concentration sensor 100 may vary oppositely. For example, the pump cell temperature decreases to 610° C. which is 190° C. lower than the target value. The cell temperature difference becomes "−150° C.". In this case, the pump cell 110 is in an inactive condition and therefore cannot operate accurately. Hence, the heater power control is performed in such a manner that the sum of cell temperatures is equalized to the target value (1,560° C.). In each cell, the temperature increases by an amount of 95° C. The sensor cell temperature becomes 855° C. and the pump cell temperature becomes 705° C. Thus, the inactive condition of the pump cell 110 is eliminated through this heater control.

As described above, both of the pump cell temperature and the sensor cell temperature fluctuate. Thus, the application voltage is controlled in accordance with the impedance of each cell. For example, according to the technique shown in FIGS. 22 and 23, it is preferable to selectively use the plurality of application voltage lines with reference to the pump cell impedance Zp.

Alternatively, it is possible to provide a plurality of a plurality of application voltage lines L11, L12 and L13 for the sensor cell 120 to selectively use an optimum application voltage line based on the sensor cell impedance Zs. For example, the application voltage line L11 is selected when the sensor cell temperature is 800° C. The application voltage line L12 is selected when the sensor cell temperature is 750° C. And, the application voltage line L13 is selected when the sensor cell temperature is 700° C. The voltage applied to the sensor cell 120 is controlled based on the selected application voltage line.

The fourth embodiment effectively eliminates the temperature difference when the temperature distribution varies due to temperatures of the cells 110 and 120. As a result, the fourth embodiment makes it possible to suppress the excessive temperature increase or decrease to the inactive temperature in respective cells 110 and 120, thereby realizing a stable gas concentration detection.

Fifth Embodiment

The fifth embodiment proposes a method for preventing the gas concentration sensing accuracy from worsening due to the impedance detection when the application voltage to the cells 110 and 120 is changed in the apparatus for detecting the pump cell impedance and the sensor cell impedance.

Figure 27:
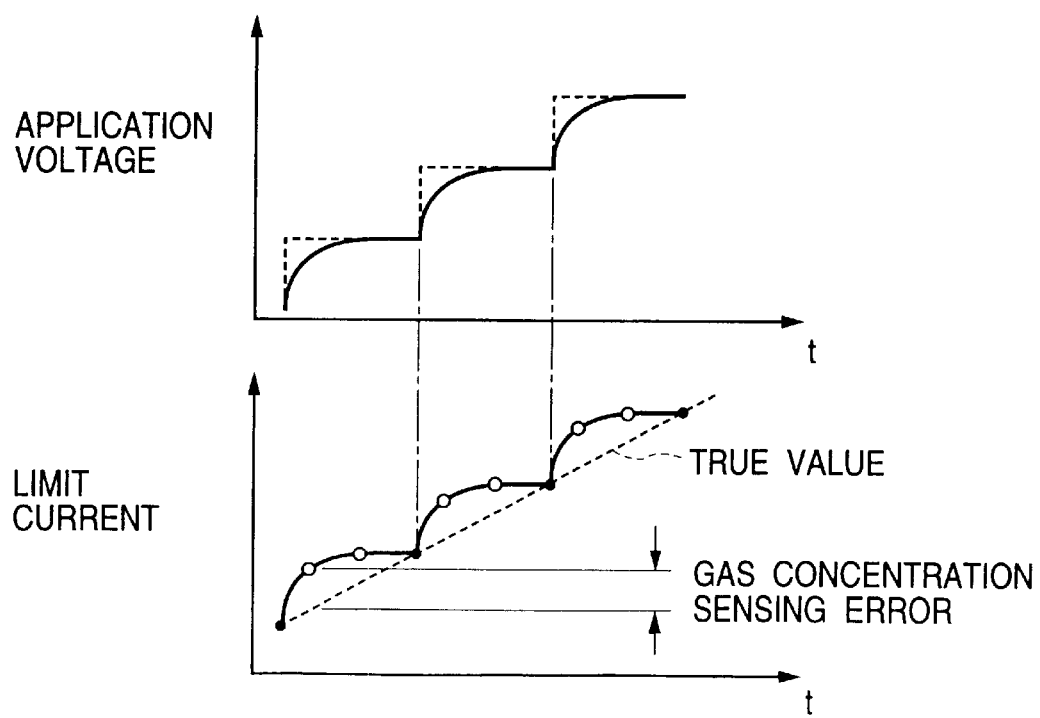
FIG. 27 is a time chart showing the transition of the application voltage and the limit current.

As described above, the command voltage (i.e., application voltage) is supplied to the gas concentration sensor 100 via the LPF (e.g., 230 or 240 shown in FIG. 16). The time constant of the LPF is set to a value suitable for the impedance detection. If this arrangement is directly used to detect a gas concentration, a large sensing error may be caused. FIG. 27 shows why the gas concentration sensing error is caused.

When the air-fuel ratio shifts from rich to lean, the command voltage supplied to each cell varies stepwise as shown by a dotted line in FIG. 27. However, after having passed the LPF, the voltage signal varies with a waveform smoothly curving at each stepwise edge of the dotted line as shown by a solid line. This makes the limit current flowing in response to the applied voltage deviate from a true value shown by the dotted line. As a result, a detected limit current value possibly includes an error. Namely, the limit current detected immediately after switching the application voltage value (shown by ● in FIG. 27) correctly represents the gas concentration. However, the limit current detected at an intermediate timing (shown by ○ in FIG. 27) deviates from the true value and therefore causes an erroneous gas concentration signal.

Figure 28:
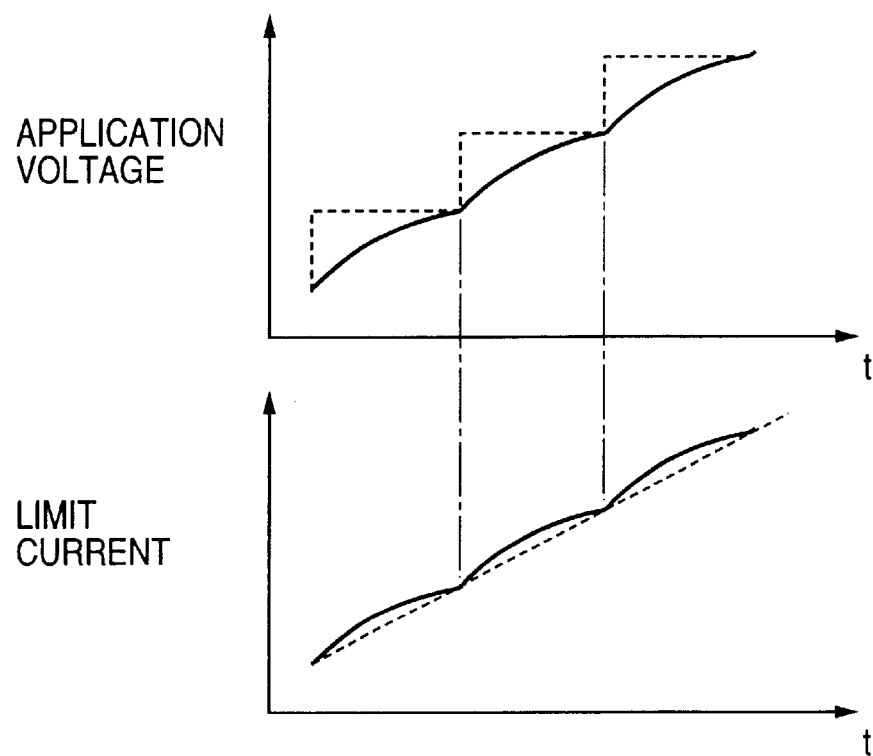
FIG. 28 is a time chart showing the transition of the application voltage and the limit current.

To solve the above-described problem, the fifth embodiment switches the LPF time constant. A time constant used for the gas concentration detection is larger than a time constant for the impedance detection. This switching operation reduces the gas concentration sensing error shown in FIG. 27. Increasing the LPF time constant means that the frequency is reduced in the change of the voltage applied to the gas concentration sensor 100. Namely, the A.C. impedance component becomes large, and the current change responsive to the application voltage change becomes small. Therefore, the deviation of the limit current from the true value becomes small as shown in FIG. 28. The gas concentration sensing error can be reduced.

Figure 29:
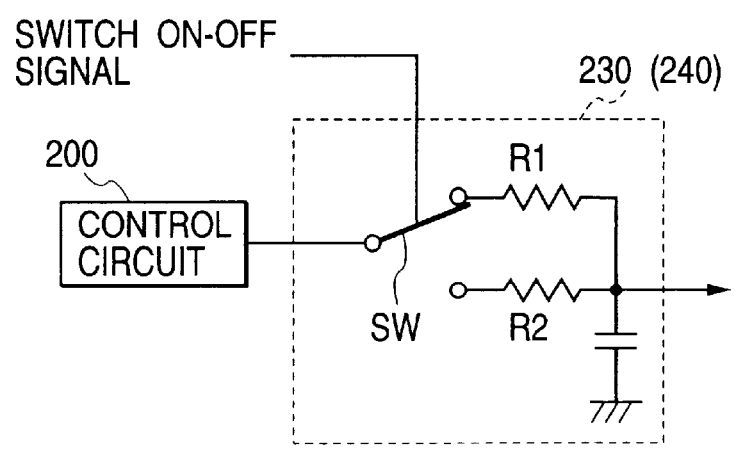
FIG. 29 is a circuit diagram showing an arrangement of a low-pass filter in accordance with a fifth embodiment of the present invention.

More specifically, the fifth embodiment selectively uses different time constants for the impedance detection and the gas concentration detection in each of LPF 230 and LPF 240 shown in FIGS. 2 and 16. FIG. 29 shows a practical arrangement of the LPF 230 and LPF 240. In FIG. 29, a switch SW is provided to selectively use a resistor R1 or a resistor R2 (R1>R2) so as to change the time constant. For example, a large time constant is selected for the gas concentration detection as shown in the drawing. A small time constant is selected for the impedance detection. It is also possible to change the time constant by varying the capacitance of a capacitor.

As described above, the fifth embodiment reduces the gas concentration sensing error. The sensing accuracy can be improved. LPF 230 and 240 serve as a speed limiting means for limiting the change speed of the application voltage. Thus, the oscillation of the application voltage can be suppressed. As another means for suppressing the oscillation of the application voltage, the control circuit 200 (CPU) can be used to limit the change speed of the application voltage. An ordinary change speed is, for example, 5 mV/4 ms. It is desirable to delay this speed to 5 mV/30 ms.

The present invention can be variously modified.

Sixth Embodiment

In the above-described first embodiment, it is possible to detect both the pump cell impedance and the sensor cell impedance. The feedback control for the heater 103 is performed based on a detected sensor cell impedance value. Meanwhile, the pump cell voltage is controlled based on a detected pump cell impedance value. According to this modification, it becomes possible to adequately manage the pump cell voltage so as to assure an oxygen concentration sensing accuracy, in addition to the effects of the first embodiment.

Seventh Embodiment

Figure 30:
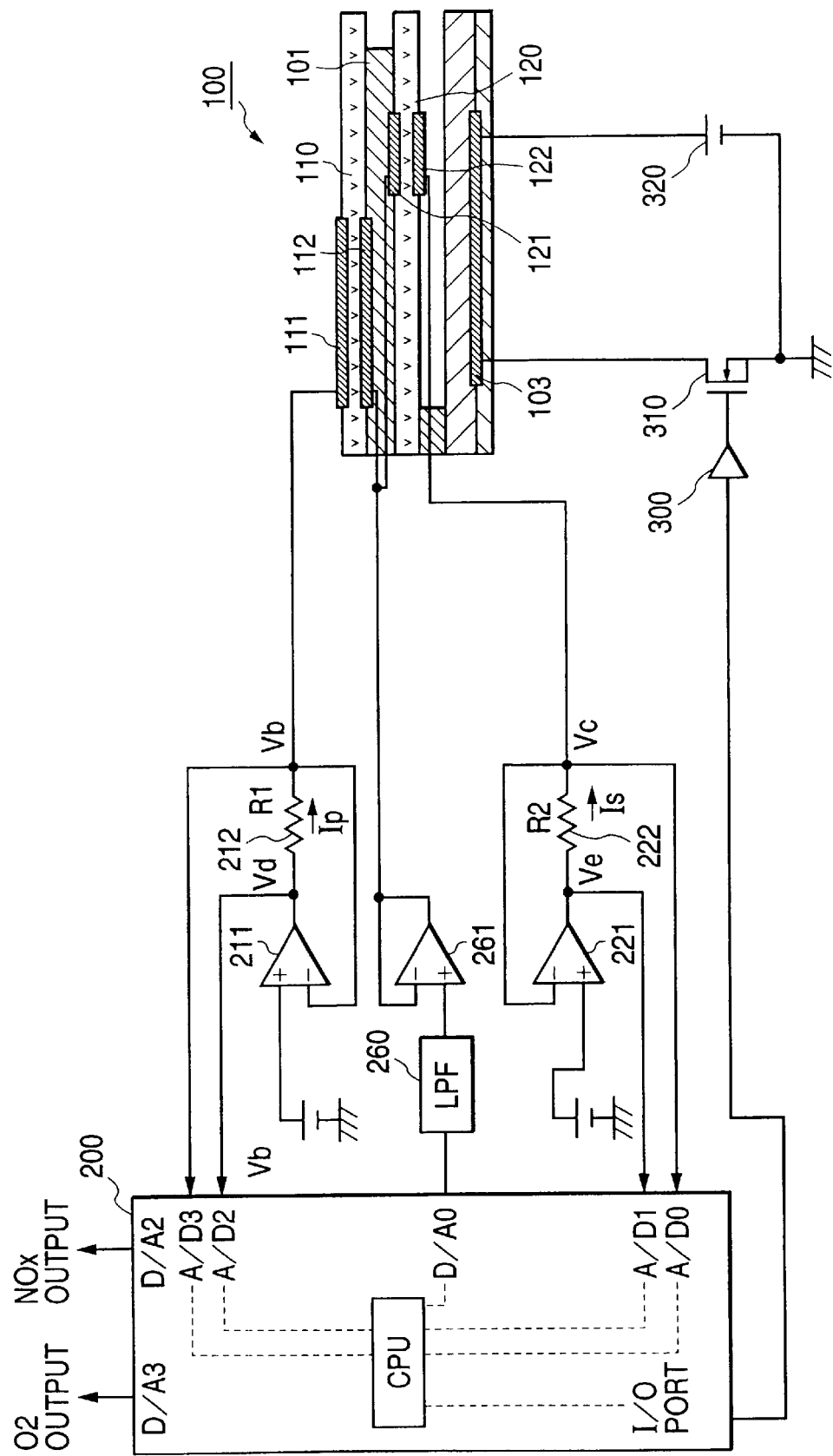
FIG. 30 is a diagram showing an overall arrangement of a gas concentration sensing apparatus in accordance with a seventh embodiment of the present invention.

The apparatus shown in FIG. 16 comprises two D/A converters and two low-pass filters for detecting both the pump cell impedance and the sensor cell impedance. To reduce the total number of components, it is possible to provide a single LPF 260 and a single amplification circuit 261 connected to the common negative terminal (i.e., reference voltage side) of the gas concentration sensor 100 as shown in FIG. 30. The command signal is produced from the converter D/A0 and sent to the LPF 260. The D/A0 output includes an A.C. component to detect the impedance of each cell. The impedance is obtainable based on a detected voltage change and a detected current change. According to this modification, it becomes possible to simplify the circuit arrangement because this arrangement requires only one D/A converter and only one LPF.

Eighth Embodiment

Figure 31:
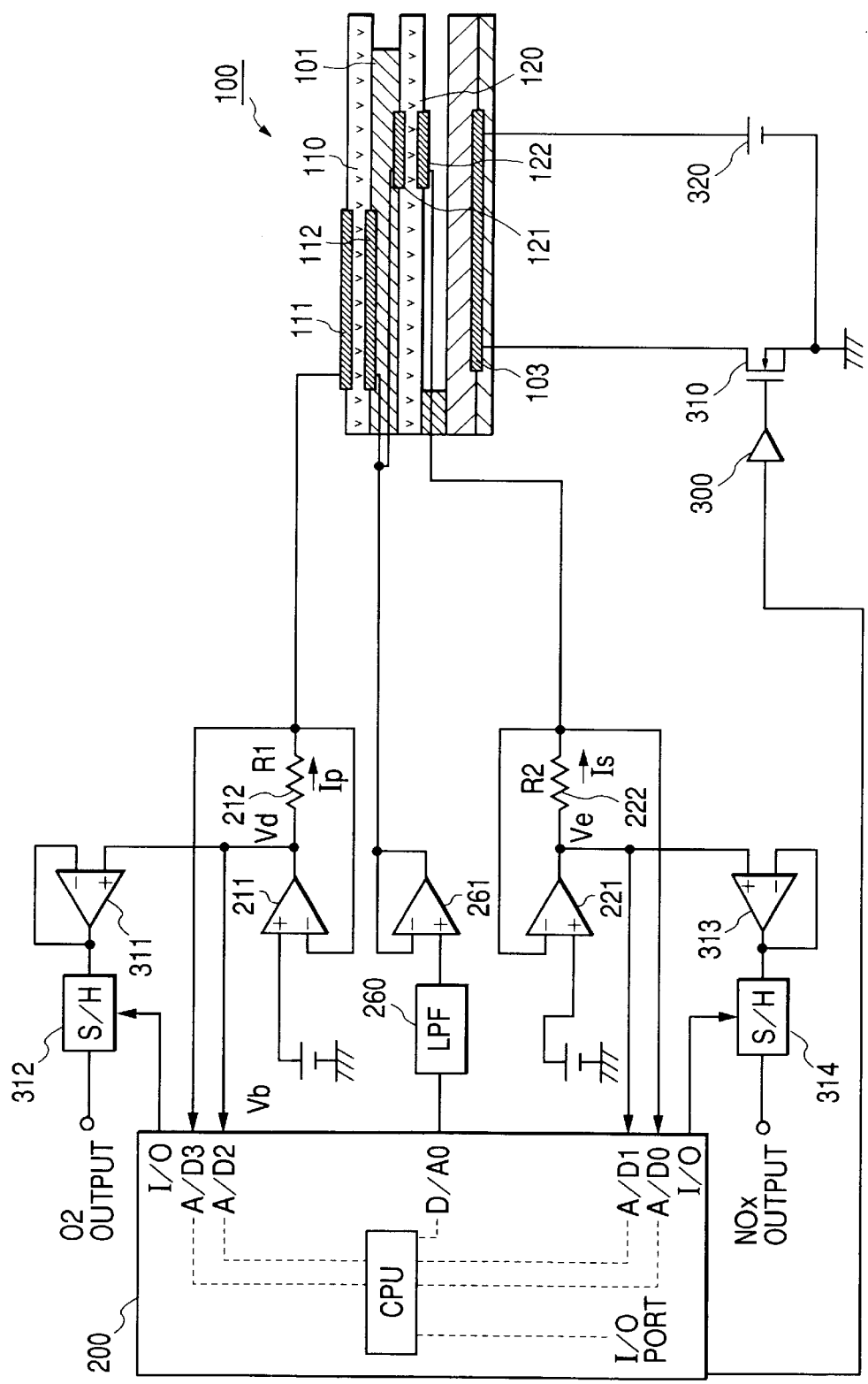
FIG. 31 is a diagram showing an overall arrangement of a gas concentration sensing apparatus in accordance with an eighth embodiment of the present invention.

FIG. 31 shows a modified arrangement of FIG. 30. An application circuit 311 and a sample hold circuit 312 are connected to the terminal Vd of the current detecting resistor 212. An application circuit 313 and a sample hold circuit 314 are connected to the terminal Ve of the current detecting resistor 222. According to this arrangement, the sample hold circuits 312 and 313 hold the latest output values detected immediately before starting the impedance detection of each cell. It becomes possible to suppress the gas concentration signal from fluctuating unwontedly. Thus, the signal output is stabilized. More specifically, a latest oxygen concentration signal is held during the pump cell impedance detection. A latest NOx concentration signal is held during the sensor cell impedance detection. The arrangement shown in FIG. 31 changes the voltage applied to the common terminal. Thus, it becomes possible to eliminate the interference between cell currents during the impedance detection.

Ninth Embodiment

According to the above-described embodiments, the common negative terminal of the pump cell 110 and the sensor cell 120 (i.e., second pump electrode 112, first sensor electrode 121) is maintained at the reference voltage Va higher than the ground potential (0V). It is however possible to modify this arrangement in the following manner. For example, only one negative terminal of the two cells (e.g., the terminal of pump cell 110 shown in FIG. 1) can be directly connected to the ground while the other negative terminal is maintained at the reference voltage level. Alternatively, it is possible to connect both of the negative terminal of the two cells to the ground.

Tenth Embodiment

The above-described embodiment provides a total of four application voltage lines as shown in FIG. 22 to selectively use one of them based on a detected pump cell impedance. It is however possible to modify this arrangement in the following manner. For example, the total number of application voltage lines selectable in the V-I characteristics shown in FIG. 22 can be reduced to three or less or can be increased to five or more. Furthermore, it is possible to prepare only one (i.e., standard) application voltage line LX1 and correct the inclination of the line LX1 in accordance with a detected pump cell impedance.

Eleventh Embodiment

The above-described embodiment performs the heater power control based on the target value equal to a sum of the pump cell impedance and the sensor cell impedance. It is however possible to perform the heater power control based on an average of the pump cell impedance and the sensor cell impedance. The same effects will be obtained.

Twelfth Embodiment

Figure 32:
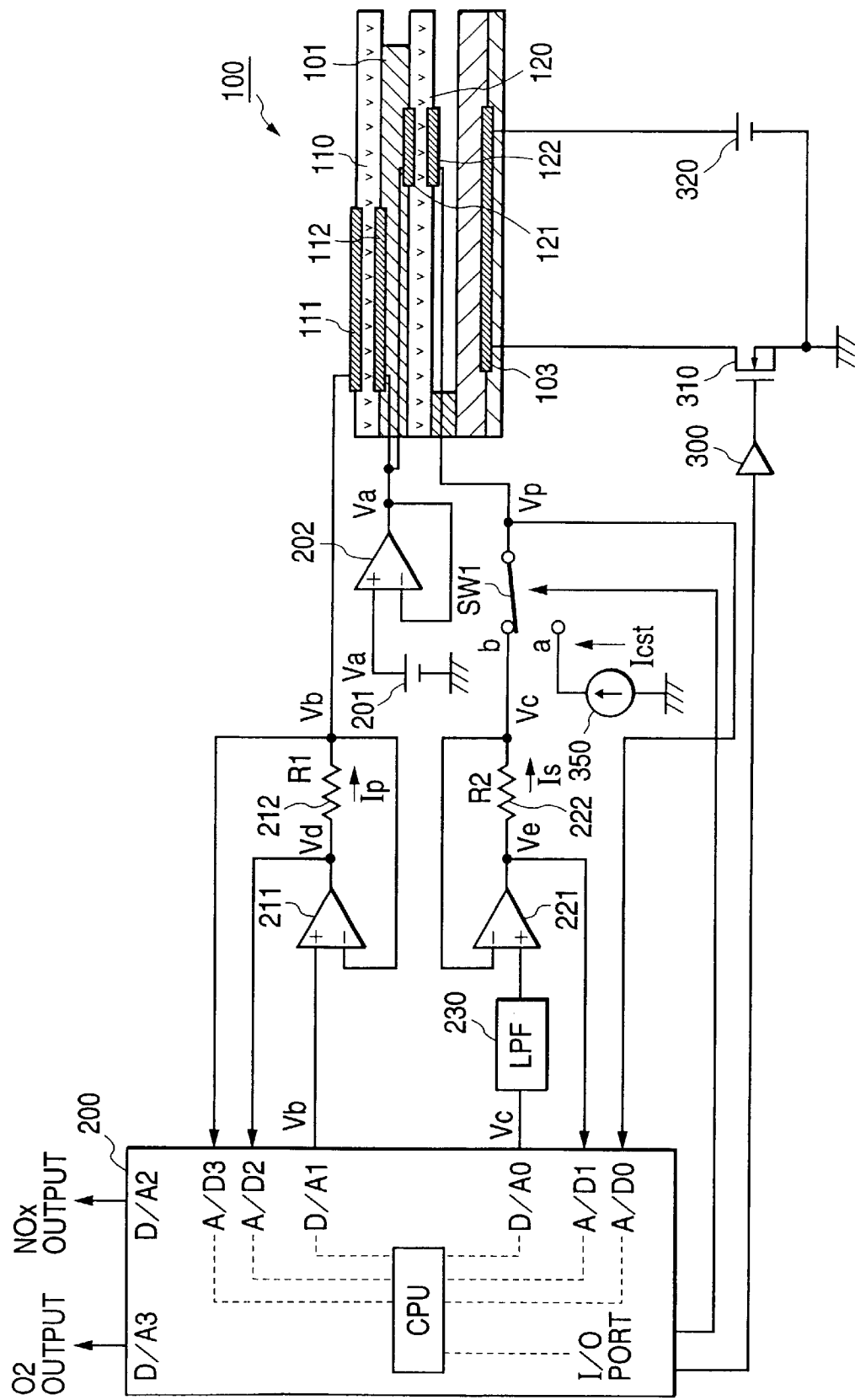
FIG. 32 is a diagram showing an overall arrangement of a gas concentration sensing apparatus in accordance with a twelfth embodiment of the present invention.

To detect the internal resistance of each cell, the above-described embodiments temporarily vary the cell voltage based on the sweep method. An A.C. impedance is measurable from a detected current change. It is however possible to use other methods. For example, it is possible to temporarily vary the cell current during the resistance detection and obtain an A.C. impedance value from a detected voltage change. FIG. 32 shows a practical arrangement as a partly-modified embodiment of FIG. 2.

FIG. 32 is different from FIG. 2 in that a switch SW1 is provided between the second sensor electrode 122 of the gas concentration sensor 100 and the current detecting resistor 222. The switch SW1 has a contact "a" connected to a constant current source 350 which produces a constant current Icst and another contact "b" connected to the current detecting resistor 222. The switch SW1 is usually connected to the contact "b." During the impedance detection, the control circuit 200 causes the switch SW1 to the contact "a" to temporarily supply the constant current Icst to the sensor cell 120. The voltage Vp is given to the second sensor electrode 122.

Figure 33:
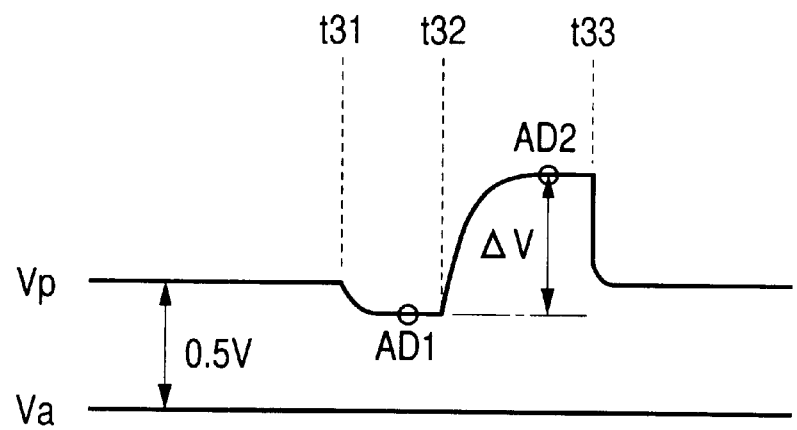
FIG. 33 is a waveform view showing a voltage change during the impedance detection in accordance with the twelfth embodiment of the present invention.

The operation of this arrangement will be explained with reference to FIG. 33. Before the time t31, the switch SW1 is connected to the contact "b" so that a voltage (e.g., Vp−Va=0.5V) is applied between the electrodes 121 and 122 of the sensor cell 120. During the period from t31 to t32, the switch SW1 is maintained in an opened condition for a predetermined time (e.g., approximately 200 μsec). A voltage Vp detectable at this moment is measured through the converter A/D0. The detected value is referred to as AD1.

At the time t32, the switch SW1 is switched to the contact "a" to supply the constant current Icst to the sensor cell 120. When a predetermined time (e.g., 25 μsec) has passed from time t32, a voltage Vp detectable at this moment is measured through the converter A/D0. The detected value is referred to as AD2. The impedance is detected from the relationship between the constant current Icst and the voltage change amount ΔV (=AD2−AD1).

Impedance=ΔV/Icst

Thereafter, at the time t33, the switch SW1 is returned to the contact "b." Regarding the impedance detection of the pump cell 110, it can be done in the same manner as in the above-described sensor cell impedance detection.

Furthermore, a D.C. element resistance is measured as the internal resistance of each cell. The heater feedback control or the application voltage control is performed based on a detected D.C. element resistance value. In practice, the D.C. element resistance is detectable in the following manner. A voltage (e.g., a negative voltage) is applied in a resistor dominant region of the sensor V-I characteristic coordinates. The D.C. element resistance is based on a detected current value (a negative current value).

Thirteenth Embodiment

Figure 34:
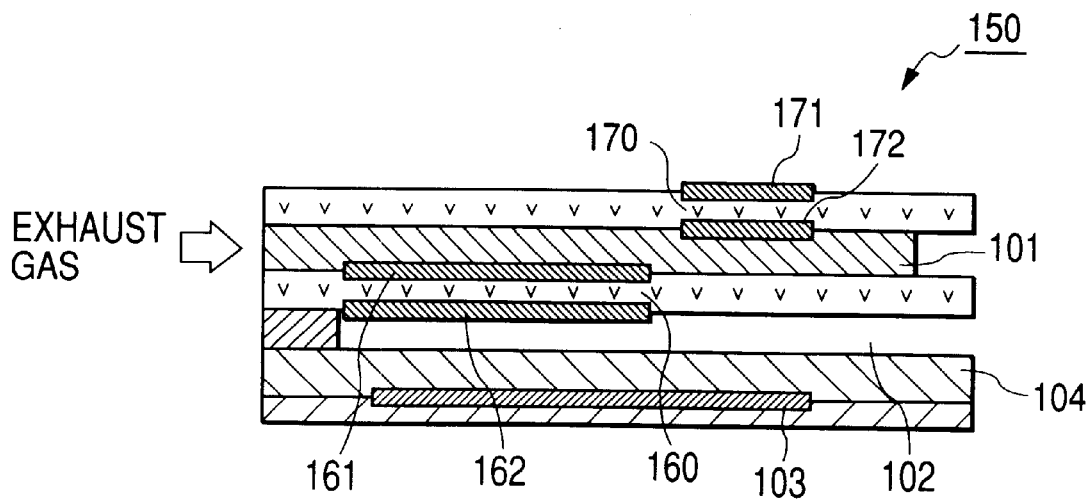
FIG. 34 is a cross-sectional view showing an arrangement of a gas concentration sensor in accordance with a thirteenth embodiment of the present invention.

The present invention is not limited to the above-described gas concentration sensor 100 and therefore can be applied, for example, to a gas concentration sensor shown in FIG. 34. The gas concentration sensor 150 shown in FIG. 34 is different from the gas concentration sensor 100 shown in FIG. 3 in that the pump cell and the sensor cell are oppositely arranged. Namely, a pump cell 160 detecting an oxygen concentration in the exhaust gas is interposed between the porous diffusive layer 101 and the atmospheric duct 102. A sensor cell 170 detecting a NOx concentration in the exhaust gas is laminated or stacked on the porous diffusive layer 101 at one side and is exposed to the exhaust gas at the other side. The pump cell 160 has first and second pump electrodes 161 and 162. The sensor cell 170 has first and second sensor electrodes 171 and 172. The first pump electrode 161, facing the porous diffusive layer 101, is made by a precious metal inactive to the NOx gas, such as Au—Pt. Namely, the first pump electrode 161 is an electrode which is unable to decompose the NOx gas. Other electrodes are made of noble metals having high catalytic activity, such as platinum. The gas concentration sensor 150 (cells 160 and 170) is similar to the above-described gas concentration sensor 100 in the gas concentration sensing-principle and in the sensor signal characteristics which are already explained and will not be explained again.

Fourteenth Embodiment

The present invention is not limited to the double-cell type gas concentration sensors explained in the above embodiments. The present invention can be applied to other gas concentration sensors which may have a triple-cell arrangement or comprises four or more cells consisting of divided pump cells and divided sensor cells. Hereinafter, a practical arrangement of the gas concentration sensing apparatus having a triple-cell arrangement will be explained.

Figure 35:
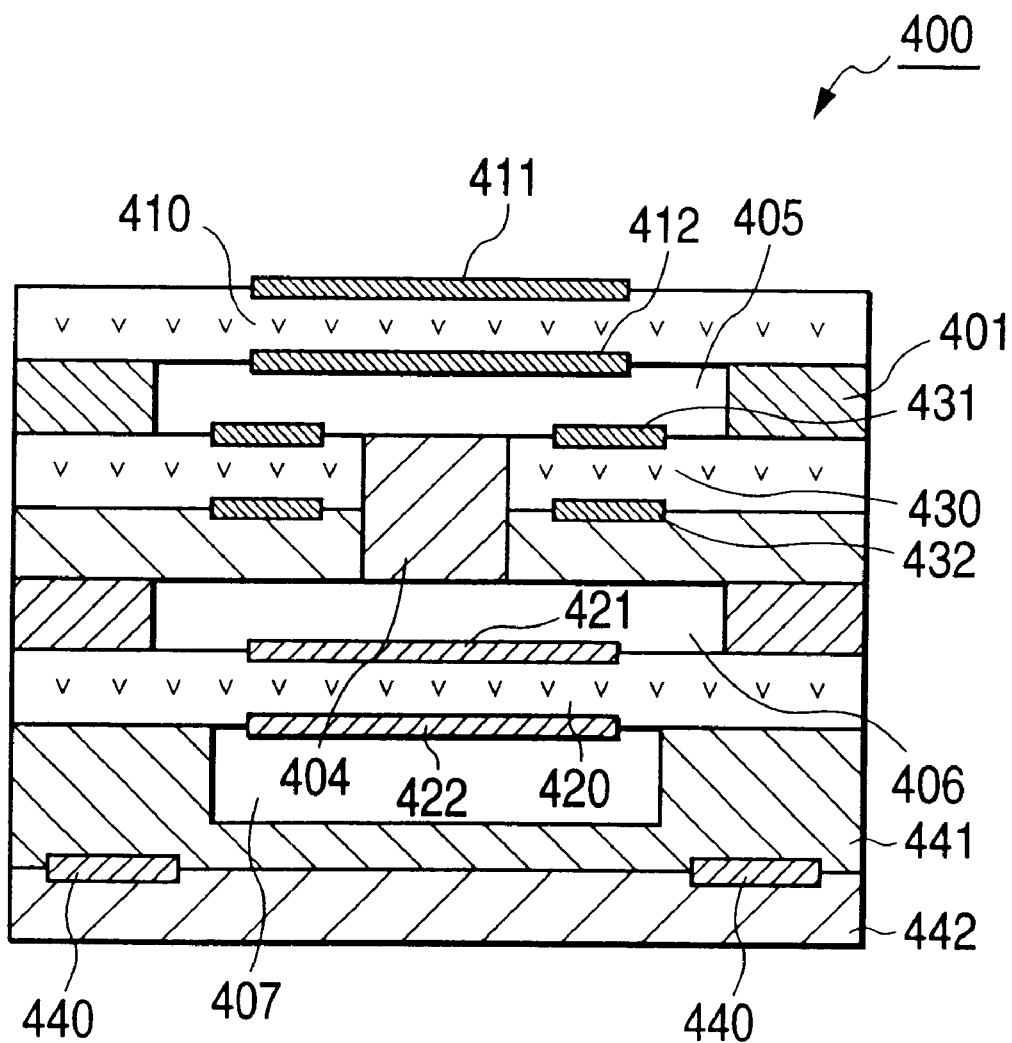
FIG. 35 is a cross-sectional view showing an arrangement of a gas concentration sensor in accordance with a fourteenth embodiment of the present invention.

FIG. 35 shows a triple-cell type gas concentration sensor 400 which chiefly comprises a pump cell 410 (i.e., first cell), a reference cell 430, a sensor cell 420 (i.e., second cell), and a heater 440. The pump cell 410 discharges the oxygen contained in the exhaust gas to detect the oxygen concentration. The reference cell 430 detects a partial pressure of the oxygen. The sensor cell 420 decomposes the NOx gas and discharges the oxygen ions to detect the NOx concentration.

The exhaust gas emitted from the engine is introduced into a first chamber 405 via a porous diffusive layer 401. The pump cell 410 discharges the oxygen from the first chamber 405 without decomposing the NOx based on a monitored voltage value of the reference cell 430. The voltage of reference cell 430 can be monitored based on a voltage difference between a first reference electrode 431 and a second reference electrode 432. Namely, the oxygen concentration is measured based on a current flowing in response to a voltage applied between a first pump electrode 411 and a second pump electrode 412.

After the excessive oxygen is discharged, the residual exhaust gas is introduced into a second chamber 406 via a second porous diffusive layer 404. The NOx gas residing in the second chamber 406 is decomposed on the sensor cell 420 and discharged. Namely, the NOx gas is discharged by applying a voltage applied between a first sensor electrode 421 and a second sensor electrode 422. The NOx concentration can be detected by measuring a current flowing in response to the voltage applied between the first sensor electrode 421 and the second sensor electrode 422.

For example, when the exhaust gas in the first chamber 405 shifts to the lean side (i.e., when the oxygen concentration increases), the electromotive force of the reference cell 430 reduces and the voltage of second reference electrode 432 reduces. In this case, the oxygen in the first chamber 405 is discharged to the exhaust gas side (i.e., the upper side of FIG. 35) via the pump cell 410. On the other hand, when the oxygen concentration in the first chamber 405 is very low, the electromotive force of the reference cell 430 increases and the voltage of second reference electrode 432 increases. In this case, an oxygen amount discharged from the first chamber 405 decreases. Thus, the oxygen concentration in the exhaust gas can be detected by measuring the pump cell current detectable at this moment.

Meanwhile, the exhaust gas is introduced into the second chamber 406 via the second porous diffusive layer 404. When a predetermined voltage is applied to the sensor cell 420, the sensor cell 420 decomposes the NOx gas and discharges the oxygen ions to an atmospheric duct 407 via the second chamber 406. Thus, the NOx concentration in the exhaust gas can be detected by measuring the sensor cell current detectable at this moment.

The heater 440 is embedded in insulation layers 441 and 442. When electric power is supplied to the heater 440, the heater 440 produces heat energy so as to activate an entire sensor body including the cells 410,420 and 430 (as well as the electrodes).

In the gas concentration sensor 400, the heater power control can be performed based on the impedance of sensor cell 420 (i.e., second cell) so as to equalize the sensor cell impedance to a constant value as explained in the first embodiment. Accordingly, the sensor cell temperature does not fluctuate due to the exhaust gas temperature change or gas flow speed change. The NOx concentration sensing accuracy does not deteriorates. Thus, it becomes possible to attain the object of the present invention. Namely, the gas concentration sensing accuracy is adequately maintained.

Alternatively, as explained in the second embodiment, it is preferable to detect each impedance of cells 410, 420 and 430, and judge the temperature condition relating to the activated condition of cells 410, 420 and 430, and further selectively perform the impedance feedback control of each cell based on the judgement result. Thus, the gas concentration sensing accuracy does not deteriorate even when respective cells have temperature characteristics different from each other due to their structures. As a result, it becomes possible to adequately maintain the gas concentration sensing accuracy regardless of the fluctuation in the cell temperature distribution.

In practice, in the beginning of the cold startup operation, the impedance feedback control is performed for the high-temperature cell among the plurality of cells 410 to 430. Subsequently, the impedance feedback control for the sensor cell 420 starts. Furthermore, when the temperature difference between cells is relatively large, the impedance feedback control is performed for the highest-temperature cell. The impedance feedback control for the sensor cell 420 is performed when the cell temperature difference is relatively small. Accordingly, when the exhaust gas temperature is stable, the impedance feedback control for the sensor cell 420 is performed. When the exhaust gas temperature increases temporarily, the impedance feedback control is performed for the cell which is most sensitively influenced by the exhaust gas temperature increase. With the above arrangement, it becomes possible to adequately maintain the gas concentration sensing accuracy regardless of the fluctuation in the cell temperature distribution.

Fifteenth Embodiment

The present invention is not limited to a gas concentration sensor capable of detecting both the oxygen concentration and the NOx concentration. For example, the present invention is applicable to a gas concentration sensor capable of detecting both the oxygen concentration and a HC or CO concentration. In the case of detecting the HC or CO concentration, the pump cell discharges excessive oxygen contained in the exhaust gas (i.e., in the measuring gas) and then the sensor cell decomposes HC or CO contained in the residual exhaust gas. Accordingly, it becomes possible to detect the HC or CO concentration in addition to the oxygen concentration.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas concentration sensing apparatus using a gas concentration sensor, said gas concentration sensor comprising:
a first cell for discharging excessive oxygen contained in a measuring gas in accordance with an applied voltage and producing a current responsive to an oxygen concentration,
a second cell producing a current responsive to a concentration of a specific component involved in the measuring gas after the excessive oxygen is discharged, and
a heater for heating said first cell and said second cell, wherein an internal resistance of said second cell is detected, and electric power supplied to said heater is controlled in accordance with a detected internal resistance value of said second cell.

2. The gas concentration sensing apparatus in accordance with claim 1, wherein an internal resistance of said first cell is detected, and said voltage applied to said first cell is controlled in accordance with a detected internal resistance value of said first cell.

3. The gas concentration sensing apparatus in accordance with claim 1, wherein the internal resistance of said second cell is detected by temporarily changing a voltage or current applied to said second cell, wherein
a sample hold circuit is provided in a signal path for outputting a sensor signal representing a detected oxygen or other gas concentration in the measuring gas, and said sample hold circuit holds a latest value of the sensor signal during the internal resistance detection of said sensor cell.

4. The gas concentration sensing apparatus in accordance with claim 1, further comprising speed limiting means for limiting a change speed of the voltage applied to said second cell.

5. A gas concentration sensing apparatus comprising:

a gas concentration sensor comprising a plurality of cells including a first cell for discharging excessive oxygen contained in a measuring gas in accordance with an applied voltage and producing a current responsive to an oxygen concentration, a second cell for producing a current responsive to a concentration of a specific component of a gas being measured after the excessive oxygen is discharged, and a heater for heating said plurality of cells;

detecting means for detecting an internal resistance of each of said plurality of cells;

judging means for judging temperature conditions of said plurality of cells; and power control means for selectively performing a heater power control based on a detected internal resistance value of said plurality of cells with reference to a judgement result of said temperature conditions.

6. The gas concentration sensing apparatus in accordance with claim 5, wherein said power control means is for performing the heater power control in a cold startup condition based on a detected internal resistance value of a highest temperature cell among said plurality of cells, and thereafter performing the heater power control based on a detected internal resistance value of said second cell.

7. The gas concentration sensing apparatus in accordance with claim 5, wherein said power control means is for performing the heater power control based on a detected internal resistance value of a highest temperature cell among said plurality of cells when there is a large temperature difference among said plurality of cells, and for performing the heater power control based on a detected internal resistance value of said second cell when there is a small temperature difference among said plurality of cells.

8. The gas concentration sensing apparatus in accordance with claim 5, further comprising voltage control means for controlling the voltage applied to said first cell based on the detected internal resistance value of said first cell.

9. The gas concentration sensing apparatus in accordance with claim 5, wherein the internal resistance of each of said plurality of cells is detected by temporarily changing a voltage or current applied to said each of said plurality of cells, wherein a sample hold circuit is provided in a signal path for outputting a sensor signal representing a detected oxygen or other gas concentration in the measuring gas, and said sample hold circuit holds a latest value of the sensor signal during the internal resistance detection of each cell.

10. The gas concentration sensing apparatus in accordance with claim 5, further comprising speed limiting means for limiting a change speed of the voltage applied to each cell.

11. A gas concentration sensing apparatus comprising:

a gas concentration sensor comprising a first cell for discharging excessive oxygen contained in a measuring gas in accordance with an applied voltage and producing a current responsive to an oxygen concentration, a second cell producing a current responsive to a concentration of a specific component involved in the measuring gas after the excessive oxygen is discharged, and a heater for heating said first cell and said second cell;

first detecting means for detecting an internal resistance of said first cell;

second detecting means for detecting an internal resistance of said second cell; and power control means for controlling electric power supplied to said heater so as to equalize a sum or an average of detected internal resistance values of said first and second cells with a target value.

12. The gas concentration sensing apparatus in accordance with claim 11, further comprising voltage control means for controlling the voltage applied to said first cell based on the detected internal resistance value of said first cell.

13. The gas concentration sensing apparatus in accordance with claim 11, wherein the internal resistance of each of the first and second cells is detected by temporarily changing a voltage or current applied to said each of the first and second cells, wherein a sample hold circuit is provided in a signal path for outputting a sensor signal representing a detected oxygen or other gas concentration in the measuring gas, and said sample hold circuit holds a latest value of the sensor signal during the internal resistance detection of each cell.

14. The gas concentration sensing apparatus in accordance with claim 11, further comprising speed limiting means for limiting a change speed of the voltage applied to each cell.

* * * * *